United States Patent
Hall et al.

(10) Patent No.: US 9,636,133 B2
(45) Date of Patent: May 2, 2017

(54) METHOD OF MANUFACTURING AN ULTRASOUND SYSTEM

(71) Applicant: The Regents of the University of Michigan, Ann Arbor, MI (US)

(72) Inventors: Timothy L. Hall, Ann Arbor, MI (US); Adam Maxwell, Seattle, WA (US); Charles A. Cain, Ann Arbor, MI (US); Yohan Kim, Ann Arbor, MI (US); Zhen Xu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 586 days.

(21) Appl. No.: 13/874,083

(22) Filed: Apr. 30, 2013

(65) Prior Publication Data
US 2013/0289593 A1  Oct. 31, 2013

Related U.S. Application Data

(60) Provisional application No. 61/640,560, filed on Apr. 30, 2012.

(51) Int. Cl.
*A61B 17/225*  (2006.01)
*H01L 41/053*  (2006.01)
(Continued)

(52) U.S. Cl.
CPC .... *A61B 17/320068* (2013.01); *A61B 17/225* (2013.01); *A61N 7/02* (2013.01);
(Continued)

(58) Field of Classification Search
CPC .......... A61B 17/225; A61B 17/320068; A61B 2017/00526; Y10T 29/42; Y10T 29/49005;
(Continued)

(56) References Cited

U.S. PATENT DOCUMENTS 3,243,497 A  3/1966  Kendall et al.
3,679,021 A  7/1972  Goldberg et al.
(Continued)

FOREIGN PATENT DOCUMENTS

DE   3220751 A1   12/1983
DE   3544628 A1   6/1987
(Continued)

OTHER PUBLICATIONS

Billson et al., Rapid Prototyping Technologies for Ultrasonic Beam Focussing in NDE, 2011 IEEE International Ultrasonic Symposium Proceedings, Oct. 2011, pp. 2472-2474.*
(Continued)

*Primary Examiner* — A. Dexter Tugbang
(74) *Attorney, Agent, or Firm* — Shay Glenn LLP

(57) ABSTRACT

An ultrasound therapy system is provided that can include any number of features. In some embodiments, the custom transducer housings can be manufactured using a rapid-prototyping method to arrange a plurality of single-element, substantially flat transducers to share a common focal point. The rapid-prototyping method can include, for example, fused-deposition modeling, 3D printing, and stereolithography. In some embodiments, the therapy system can include a plurality of transducer modules insertable into the openings of the transducer housing. Methods of manufacture are also described, including designing a transducer housing shell to a desired geometry and a plurality of acoustic focusing lenses integral to the transducer housing shell in a 3D computer aided design software, and constructing the transducer housing shell and the plurality of acoustic focusing lenses integral to the transducer housing shell using a rapid-prototyping method.

6 Claims, 21 Drawing Sheets

(51) Int. Cl.

| | | |
|---|---|---|
| *A61B 17/32* | (2006.01) | |
| *H01L 41/04* | (2006.01) | |
| *H01L 41/23* | (2013.01) | |
| *H01L 41/25* | (2013.01) | |
| *A61N 7/02* | (2006.01) | |
| *G10K 11/00* | (2006.01) | |
| *G01N 29/22* | (2006.01) | |
| *G01N 29/24* | (2006.01) | |
| *A61B 17/00* | (2006.01) | |
| *A61N 7/00* | (2006.01) | |

(52) U.S. Cl.
CPC ............ G10K 11/004 (2013.01); H01L 41/04 (2013.01); H01L 41/053 (2013.01); H01L 41/23 (2013.01); H01L 41/25 (2013.01); *A61B 2017/00526* (2013.01); *A61N 2007/006* (2013.01); *A61N 2007/0039* (2013.01); *A61N 2007/0065* (2013.01); *A61N 2007/0091* (2013.01); *A61N 2007/0095* (2013.01); *G01N 29/223* (2013.01); *G01N 29/225* (2013.01); *G01N 29/226* (2013.01); *G01N 29/2437* (2013.01); *Y10T 29/42* (2015.01); *Y10T 29/49005* (2015.01); *Y10T 29/49007* (2015.01)

(58) Field of Classification Search
CPC ...... Y10T 29/49007; A61N 2007/0039; A61N 2007/006; A61N 2007/0065; A61N 2007/0091; A61N 2007/0095; A61N 7/02; G10K 11/004; G01N 29/223; G01N 29/225; G01N 29/226; G01N 29/2437; H01L 41/04; H01L 41/053; H01L 41/23; H01L 41/25

See application file for complete search history.

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,176,842 B1 | 1/2001 | Tachibana et al. |

(56) References Cited

U.S. PATENT DOCUMENTS

| | | | |
|---|---|---|---|
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 * | 3/2003 | Scanlon ............... G10N 29/226 |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 8,057,408 B2 | 11/2011 | Cain et al. |
| 8,333,115 B1 * | 12/2012 | Garvey et al. ........ G01N 29/225 |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 * | 3/2007 | Sarr .................... G01N 29/225 |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2010/0011845 A1 | 1/2010 | Laugharn et al. |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0163694 A1 | 7/2010 | Fadler et al. |
| 2010/0261994 A1 | 10/2010 | Davalos et al. |
| 2010/0274136 A1 * | 10/2010 | Cerofolini ............ H01L 41/053<br>600/459 |
| 2010/0286519 A1 | 11/2010 | Lee et al. |
| 2010/0305432 A1 | 12/2010 | Duhay et al. |
| 2010/0317971 A1 | 12/2010 | Fan et al. |
| 2011/0040190 A1 | 2/2011 | Jahnke et al. |
| 2011/0054315 A1 | 3/2011 | Roberts et al. |
| 2011/0054363 A1 | 3/2011 | Cain et al. |
| 2011/0067624 A1 | 3/2011 | Cain et al. |
| 2011/0112400 A1 | 5/2011 | Emery et al. |
| 2011/0118602 A1 | 5/2011 | Weng et al. |

(56) References Cited

U.S. PATENT DOCUMENTS

| | | |
|---|---|---|
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2012/0010541 A1 | 1/2012 | Cain et al. |
| 2012/0029353 A1 | 2/2012 | Slayton et al. |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0172720 A1 | 7/2012 | Kawabata |
| 2012/0189998 A1 | 7/2012 | Kruecker et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0041293 A1 | 2/2013 | Cain |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2014/0058293 A1 | 2/2014 | Hynynen et al. |
| 2014/0128734 A1 | 5/2014 | Genstler et al. |
| 2015/0290477 A1 | 10/2015 | Jahnke et al. |

FOREIGN PATENT DOCUMENTS

| | | | |
|---|---|---|---|
| DE | 3817094 A1 | | 11/1989 |
| DE | 4012760 A1 | | 5/1992 |
| EP | 0017382 A1 | | 10/1980 |
| EP | 0320303 A2 | | 6/1989 |
| EP | 0332871 A2 | | 9/1989 |
| EP | 0384831 A2 | | 8/1990 |
| EP | 0755653 A1 | | 1/1997 |
| EP | 1374785 A1 | | 1/2004 |
| EP | 1504713 A1 | | 2/2005 |
| EP | 2397188 A1 | | 12/2011 |
| GB | 2099582 A | | 12/1982 |
| JP | 60-80779 A | | 5/1985 |
| JP | 61-196718 A | | 8/1986 |
| JP | HEI 2-215451 | | 8/1990 |
| JP | 06194347 A | * | 7/1994 |
| JP | HEI 6-197907 A | | 7/1994 |
| JP | HEI 7-504339 A | | 5/1995 |
| JP | 08-84740 A | | 4/1996 |
| JP | 06-304178 A | | 5/1996 |
| JP | 08-131454 A | | 5/1996 |
| JP | 09-55571 A | | 2/1997 |
| JP | HEI 10-512477 | | 12/1998 |
| JP | 2003-510159 A | | 3/2003 |
| JP | 2004-505660 A | | 2/2004 |
| JP | 2007520307 A | | 7/2007 |
| JP | 2010029650 A | | 2/2010 |
| JP | 2004-512502 A | | 4/2014 |
| WO | WO 94/06355 A1 | | 3/1994 |
| WO | WO 02/32506 A1 | | 4/2002 |
| WO | WO2005/018469 A1 | | 3/2005 |
| WO | WO 2008/051484 A2 | | 5/2008 |
| WO | WO2011/040054 A1 | | 7/2011 |
| WO | WO 2011/092683 A1 | | 8/2011 |
| WO | WO2011/154654 A2 | | 12/2011 |

OTHER PUBLICATIONS

Xu et al.; U.S. Appl. No. 14/046,024 entitled "Bubble-induced color doppler feedback during histotripsy," filed Oct. 4, 2013.

Bjoerk et al.; Cool/MOS CP—How to make most beneficial use of the generation of super junction technology devices. Infineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument).

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Clasen et al.; MR-guided radiofrequency ablation of hepatocellular carcinoma: Long-term effectiveness; J Vasc Interv Radiol; 22(6); pp. 762-770; Jun. 2011.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Emelianov et al.; Triplex ultrasound: Elasticity imaging to age deep venous thrombosis; Ultrasound Med Biol; 28(6); pp. 757-767; Jun. 2002.

Hynynen et al.; Tissue thermometry during ultrasound exposure; European Urology; 23(Suppl 1); pp. 12-16; 1993 (year of pub. sufficiently earlier than effective US filing date and any foreign priority date).

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Konofagou; Quo vadis elasticity imaging?; Ultrasonics; 42(1-9); pp. 331-336; Apr. 2004.

Kruse et al.; Tissue characterization using magnetic resonance elastography: Preliminary results; Phys. Med. Biol; 45(6); pp. 1579-1590; Jun. 2000.

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Nightingale et al.; Analysis of contrast in images generated with transient acoustic radiation force; Ultrasound Med Biol; 32(1); pp. 61-72; Jan. 2006.

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Rowland et al.; MRI study of hepatic tumours following high intensity focused ultrasound surgery; British Journal of Radiology; 70; pp. 144-153; Feb. 1997.

Sapareto et al.; Thermal dose determination in cancer therapy; Int J Radiat Oncol Biol Phys; 10(6); pp. 787-800; Apr. 1984.

Souchon et al.; Visualisation of HIFU lesions using elastography of the human prostate in vivo: Preliminary results; Ultrasound Med. Biol; 29(7); pp. 1007-1015; Jul. 2003.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

(56) References Cited

OTHER PUBLICATIONS

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clement et al.; A hemisphere array for non-invasive ultrasound brain therapy and surgery; Physics in Medicine and Biology, vol. 45, p. 3707-3719, Dec. 2000.

Desilets et al.; The Design of Efficient Broad-Band Piezoelectric Transducers; Sonics and Ultrasonics, IEEE Transactions on, vol. 25, pp. 115-125, May 1978.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasound Symposium, Sep. 18-21, 2005, pp. 1732-1734.

Hartmann; Ultrasonic properties of poly(4-methyl pentene-1), Journal of Applied Physics, vol. 51, pp. 310-314, Jan. 1980.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.

Kim et al.; Dependence of particle volume fraction on sound velocity and attenuation of EPDM composites; Ultrasonics, vol. 46, pp. 177-183, Feb. 2007.

Krimholtz et al.; New equivalent circuits for elementary piezoelectric transducers; Electronics Letters, vol. 6, pp. 398-399, Jun. 1970.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al; Effect of Radial Displacement of Lens on Response of Focused Ultrasonic Transducer; Japanese Journal of Applied Physics, vol. 46, p. 3077-3085; May 15, 2007.

Maréchal et al; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.

Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Roy et al.; A precise technique for the measurement of acoustic cavitation thresholds and some preliminary results; Journal of the Acoustical Society of America; vol. 78(5); pp. 1799-1805; Nov. 1985.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

(56) References Cited

OTHER PUBLICATIONS

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Teofilovic, Dejan; U.S. Appl. No. 13/446,783 entitled "Systems and Methods for Obtaining Large Creepage Isolation on Printed Circuit Boards," filed Apr. 13, 2012.

Cannata et al.; U.S. Appl. No. 14/323,693 entitled "Histotripsy excitation sequences optimized for bubble cloud formation using shock scattering," filed Jul. 3, 2014.

Cain et al.; U.S. Appl. No. 13/943,621 entitled "Devices and Methods for Using Controlled Bubble Cloud Cavitation in Fractionating Urinary Stones," filed Jul. 16, 2013.

Teofilovic et al.; U.S. Appl. No. 14/024,394 entitled "Histotripsy Therapy System," filed Sep. 11, 2013.

Lin et al.; U.S. Appl. No. 14/656,633 entitled "Frequency compounding ultrasound pulses for imaging and therapy," filed Mar. 12, 2015.

Avtech; AVR-8 Data sheet; May 23, 2004; 3 pages; retrieved from the internet (http//www.avtechpulse.com).

Cain; U.S. Appl. No. 14/845,059 entitled "Lesion generation through bone using histotripsy therapy without aberration correction," filed Sep. 3, 2015.

Arani et al.; Transurehral prostate magnetic resonance elestography; prospective imaging requirements; Magn. Reson. Med.; 65(2); pp. 340-349; Feb. 2011.

Avago Technologies; Avago's ACNV2601 optocoupler is an optically coupled logic gate; Data Sheet; 2 pages; Jul. 29, 2010.

Maxwell et al.; Cavitation clouds created by shock scattering from bubbles during histotripsy; J. Acoust. Soc. Am.; 130(4); pp. 1888-1898; Oct. 2011.

Hoebarth et al.; Color flow doppler sonography for extracorporal shock wave lithotripsy; Journal of Urology; 150(6); pp. 1768-1770; Dec. 1, 1993.

Maxwell et al.; In-vivo study of non-invasive thrombolysis by histotripsy in a porcine model; IEEE international Ultrasonics Symposium; IEEE; p. 220-223; Sep. 20, 2009.

Urban et al.; Measurement of prostate viscoelasticity using shearwave dispersion ultrasound vibrometry (SDUV): an in vitro study; IEEE International Ultrasonics Syposium Proceedings (IUS); pp. 1141-1144; Oct. 11, 2010.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Miller et al.; Real-time elastography-based monitoring of histotripsy tissue fractionation using color doppler; Ultrasonics Symposium (IUS); 2012 IEEE International; 8 pages; Oct. 7-10, 2012.

* cited by examiner

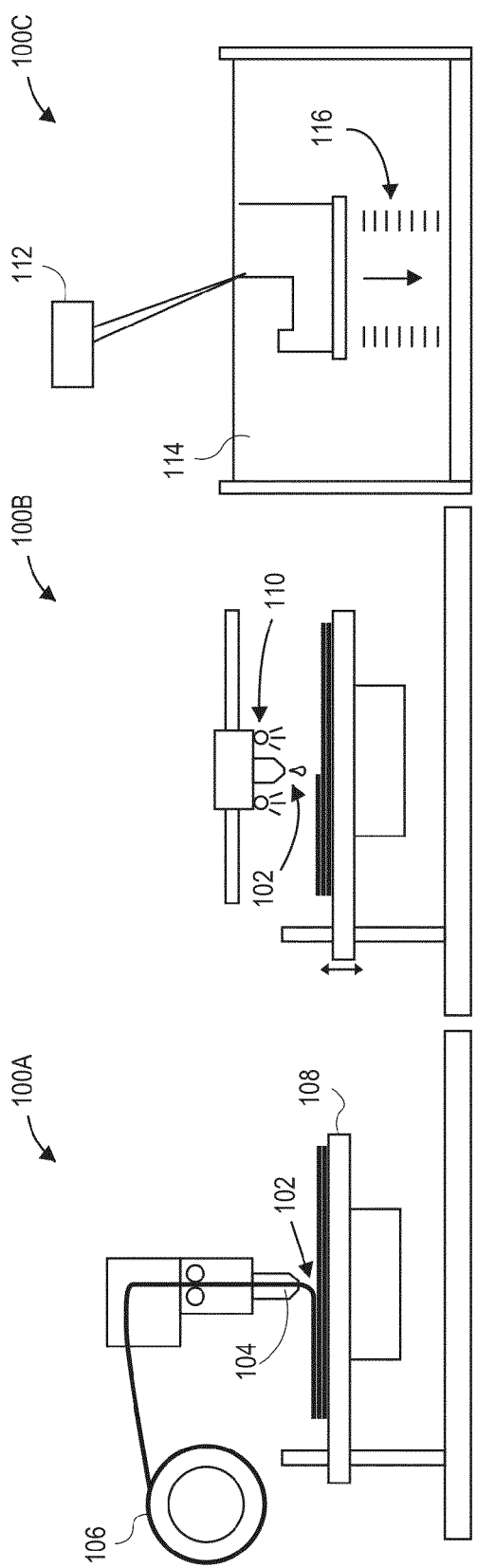

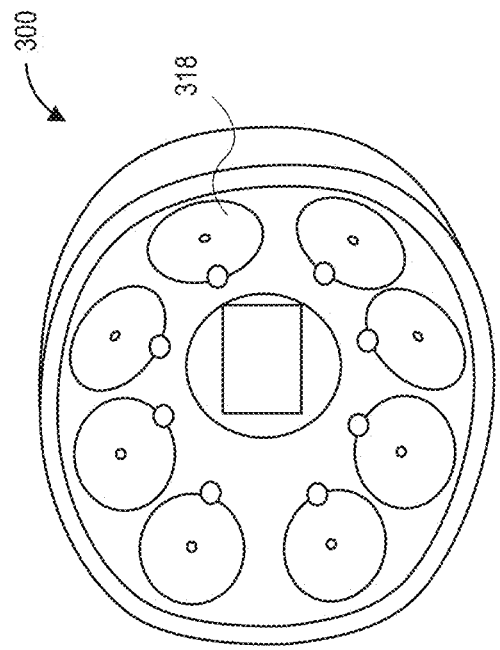
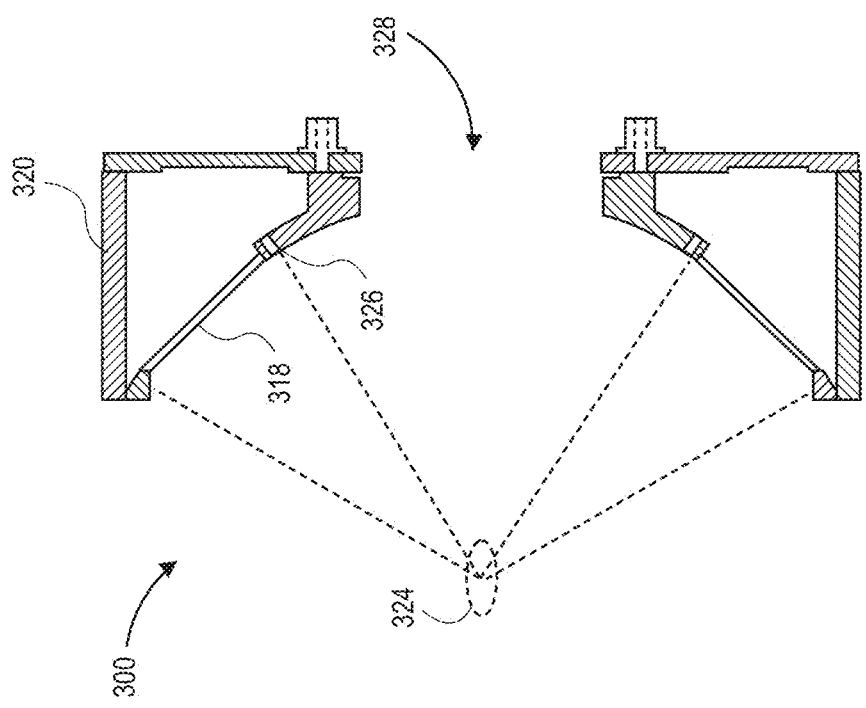

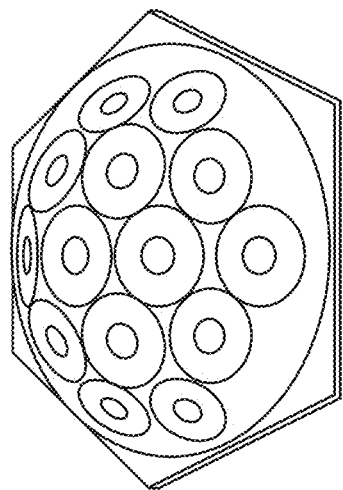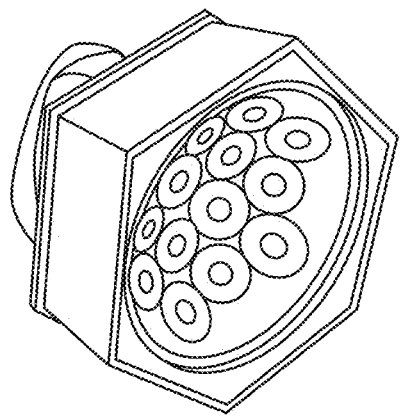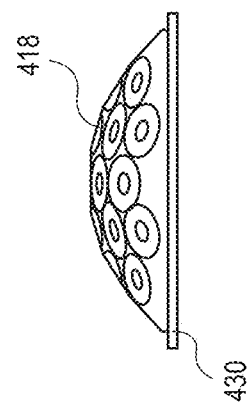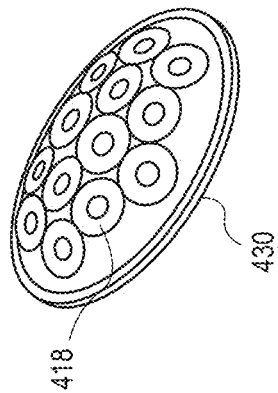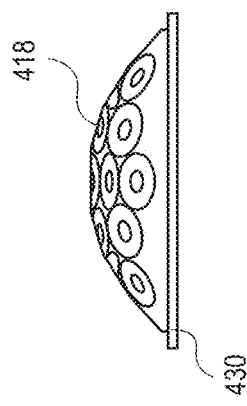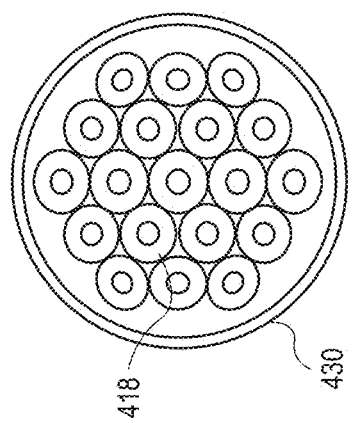

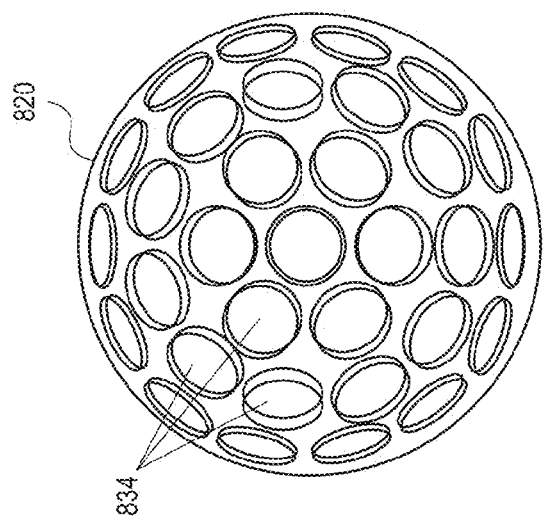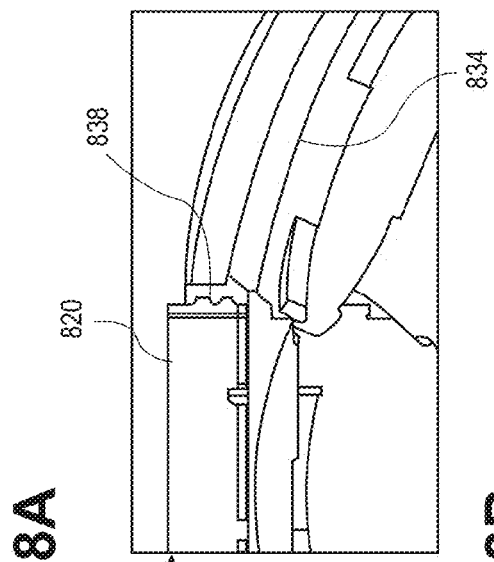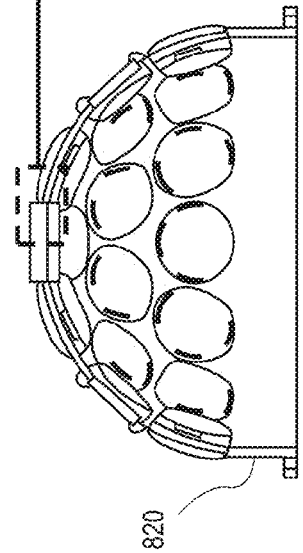
FIG. 8A
FIG. 8B

Fig. 12A No Cable No Voltage Network

Fig. 12B 2-meter Cable No Voltage Network

Fig. 12C 2-meter Cable Voltage Network

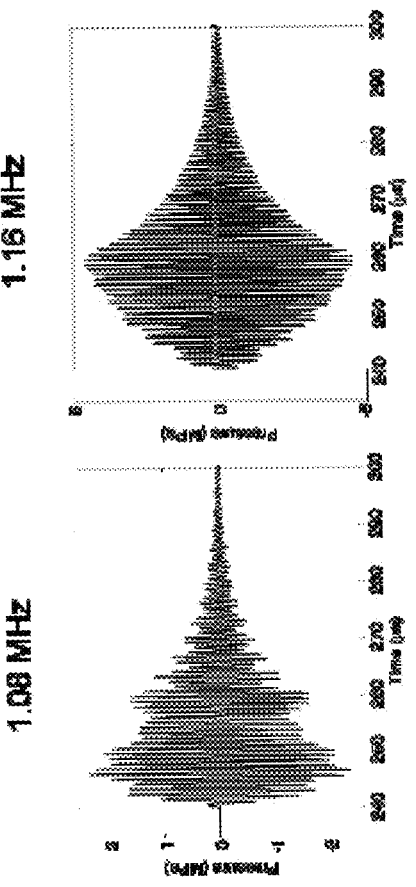
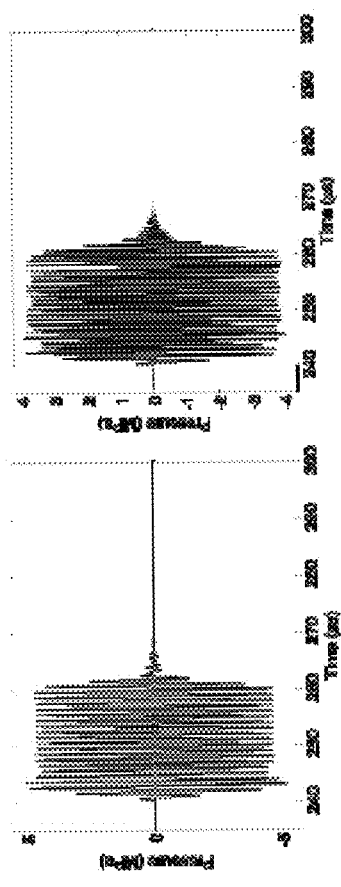
Fig. 14A  Fig. 14B  Fig. 14C
0.88 MHz  1.08 MHz  1.16 MHz
Fig. 14D  Fig. 14E  Fig. 14F
No Matching Layer/Lens
Matching Layer/Lens

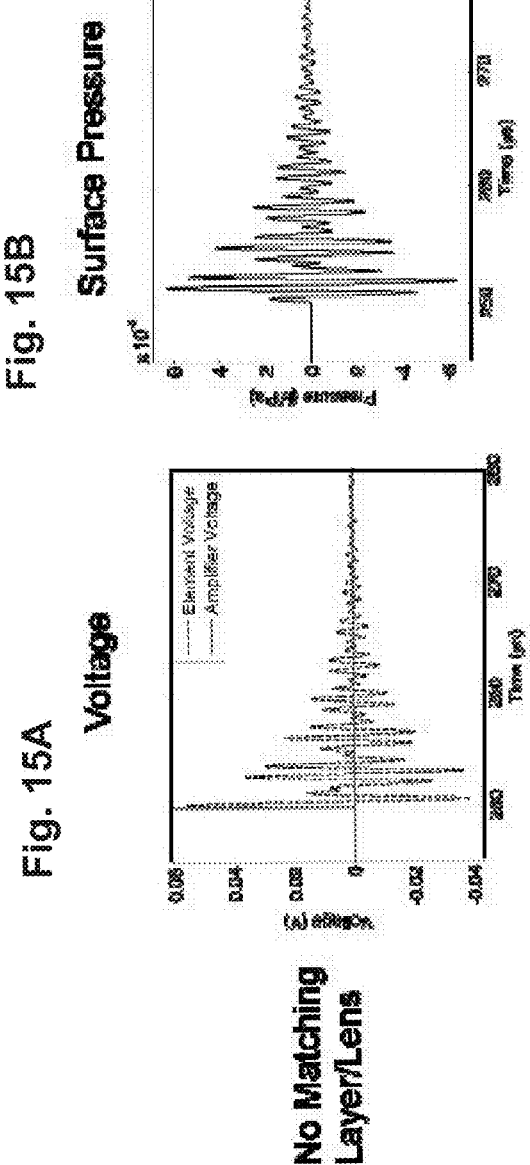
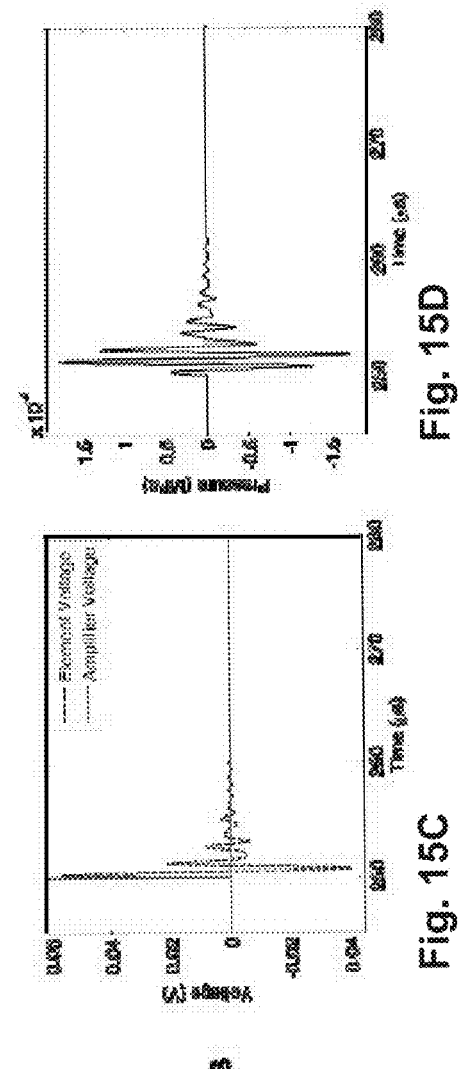
Fig. 15A Voltage — No Matching Layer/Lens
Fig. 15B Surface Pressure
Fig. 15C Matching Layer/Lens
Fig. 15D

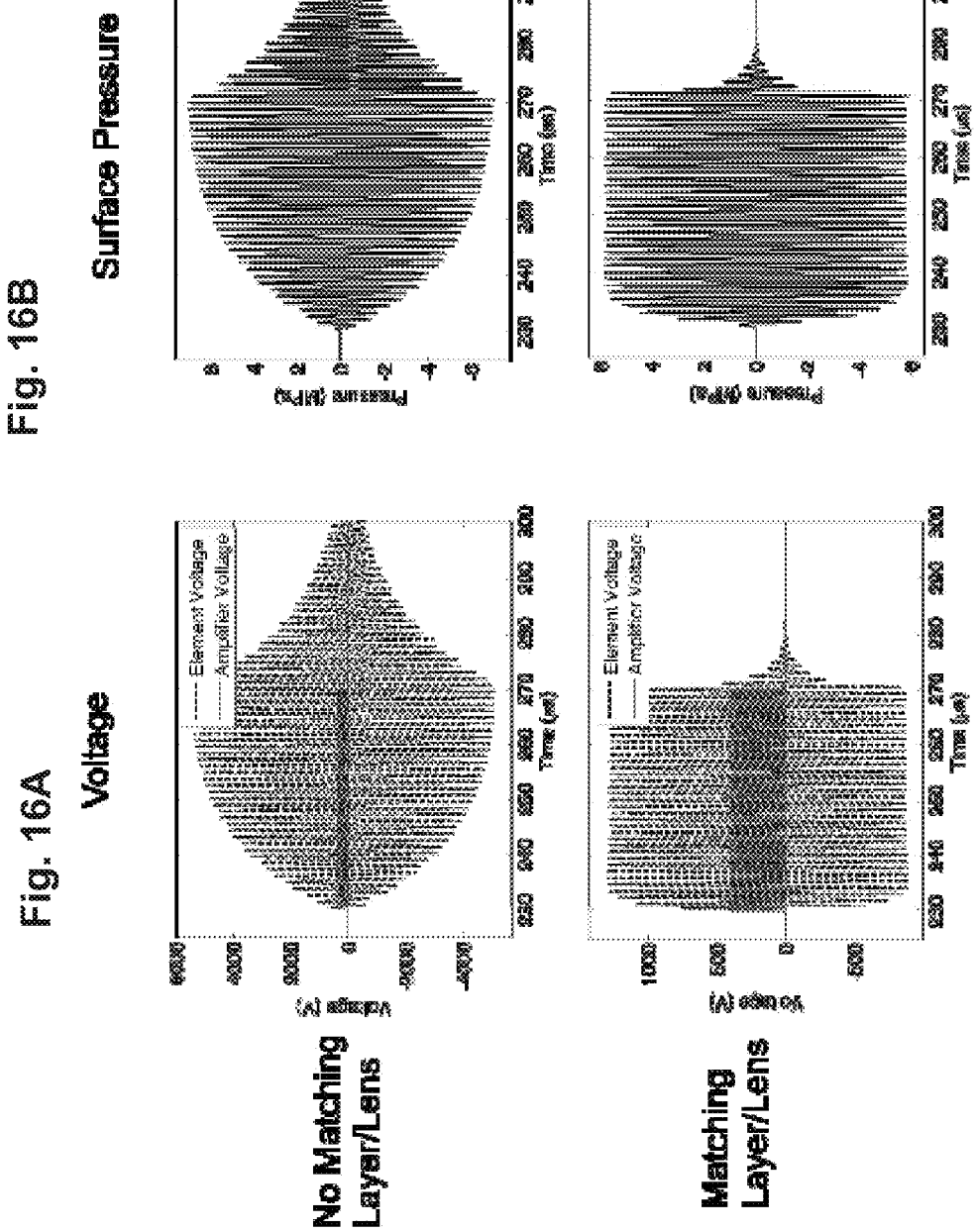

METHOD OF MANUFACTURING AN ULTRASOUND SYSTEM

CROSS REFERENCE TO RELATED APPLICATIONS

This application claims the benefit under 35 U.S.C. 119 of U.S. Provisional Patent Application No. 61/640,560, filed Apr. 30, 2012, titled "Ultrasound Transducer Manufacturing Using Rapid Prototyping Method", which application is incorporated by reference as if fully set forth herein.

GOVERNMENT RIGHTS

This invention was made with government support under Grant Nos. R01 CA134579 and R01 EB008998 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure generally relates to manufacturing high intensity focused ultrasound transducers and their designs. More specifically, the present disclosure describes manufacturing ultrasound therapy transducer and related designs such as histotripsy transducers using rapid-prototyping methods including stereolithography.

BACKGROUND

Focused ablative ultrasound therapies, such as high-intensity focused ultrasound (HIFU) thermal therapy and histotripsy, have demonstrated precise surgical destruction of pathological tissues noninvasively. These therapies rely on focused transducers to deliver high acoustic intensity or pressure to a localized region to ablate the tissue of interest. HIFU requires that a sufficient acoustic intensity be delivered to the focal region for a sufficient time to cause tissue necrosis through heating. For histotripsy, high-pressure, short duration acoustic pulses are applied to cause mechanical breakdown of tissue in the focal volume by inciting cavitation clouds or bubbles through boiling. Histotripsy requires focal pressure levels of 10 to >25 MPa peak negative pressure, and the peak positive pressure can exceed 100 MPa.

In order to generate such pressure levels, careful consideration is required for design of the therapy transducers. Transducers are most commonly constructed from piezoceramic or piezocomposite materials, using spherically curved segments which produce ideal focusing. Typical resonant frequencies vary from 500 kHz to 4 MHz depending on the application. Therapy transducers can range from simple single element construction, to phased arrays of several hundred individual elements to facilitate focal steering. Histotripsy transducers used in previous work have been constructed from piezoceramic or piezocomposite elements which are air-backed and contain a single quarter-wavelength matching layer. These transducers must be large compared to the wavelength to have considerable focal pressure gain. This stipulation can cause significant difficulty when constructing very large, curved transducers which must necessarily maintain high accuracy along the curvature of the surface.

While these transducers have been fairly reliable, they have limited geometric specifications, cost $5,000-$50,000, and require between 1.5-6 months for construction. This turnaround makes it difficult to iterate designs and make small changes to optimize the transducers. It is often desirable to form complex geometries for therapy transducers, for integration and alignment of imaging feedback probes, alignment of multiple therapy elements, generation of complex focal patterns, or maximal utilization of an available acoustic window in the body. Iteration of such transducer designs can be costly and time consuming at the research level due to the associated cost and lead time for producing focused piezoelectric elements and machining required for suitable transducer housings.

This disclosure describes novel designs and methods to construct a focused ultrasound transducer using rapid-prototyping. The transducer comprises multiple flat or high f-number piezoceramic or piezoelectric elements housed in a shell containing acoustic focusing lens and acoustic matching layer, all made using rapid-prototyping. Rapid-prototyping is gaining acceptance in engineering practice as a method to evaluate functional and nonfunctional components in research as an alternative to machining. Rapid-prototyping has advantage over subtractive (e.g., machining) or formative (e.g., injection molding) processes in that it is cost-effective, fast, and can produce nearly limitless complexity. This method can be used to construct single focused transducers as well as array transducers.

Common methods of rapid-prototyping include stereolithography, selective laser sintering, fused deposition modeling (FDM), and 3D printing. Materials used in such machines can be conventional and proprietary polymers, elastomers, plaster, ceramic composites, and metals. The accuracy and resolution of the machines is dictated by their technology. For instance, a stereolithography apparatus (SLA) system can produce resolution in all dimensions between 10-100 µm. This accuracy has been found to be precise enough to align ultrasound elements in the low MHz range.

SUMMARY OF THE DISCLOSURE

An ultrasound therapy system is provided, comprising a rapid-prototyping transducer housing, and a plurality of substantially flat, single-element transducers supported by the transducer housing, the transducers being physically separated from another by the transducer housing and arranged on the housing so as to share a common focal point, the plurality of transducers being configured to apply therapeutic ultrasound energy to tissue positioned at the focal point.

In some embodiments, the plurality of transducers comprise spherical single-element transducers. In other embodiments, the plurality of transducers comprise piezoelectric transducer elements. In one embodiment, the piezoelectric transducer elements comprise Lead-Zirconate Titanate (PZT) Ceramic.

In some embodiments, the system further comprises an acoustic lens disposed in front of each of the plurality of transducers. In some embodiments, each acoustic lens is integral to the rapid-prototyping transducer housing.

In some embodiments, the system further comprises a matching layer disposed between each transducer and acoustic lens, the matching layers being configured to acoustically couple the transducers to the acoustic lenses. In some embodiments, the matching layers comprise tapered matching layers.

In another embodiment, the housing further comprises a plurality of matching layer standoffs that separate a front surface of each transducer from a rear surface of each acoustic lens a proper distance for the matching layers.

In one embodiment, the rapid-prototyping transducer housing is manufactured from a process selected from the group consisting of fused-deposition modeling, 3D printing, and stereolithography.

In some embodiments, each of the plurality of transducers is disposed in a separate transducer module, wherein the housing comprises a plurality of openings configured to receive the transducer modules. In one embodiment, the transducer modules comprise threads and are configured to screw into the openings of the housing. In another embodiment, the openings of the housing comprise grooves adapted to mate with the threads of the transducer modules.

In some embodiments, the transducer modules each comprise an integral acoustic lens and at least one matching layer standoff that defines a space for a matching layer between the acoustic lens and the transducer.

Another ultrasound therapy system is provided, comprising a transducer housing comprising a plurality of openings, and a plurality of transducer modules configured to be inserted into the openings of the transducer housing so as to be held by the housing, each transducer module comprising an acoustic lens, a substantially flat, single-element transducer, and a matching layer disposed between the lens and the transducer, the openings of the transducer housing being arranged so as to align the single-element transducers to share a common focal point, wherein the single-element transducers are configured to apply therapeutic ultrasound energy to tissue positioned at the focal point.

In some embodiments, the transducer modules are configured to be screwed into the openings of the housing.

In other embodiments, the transducer housing comprises a concave housing.

In one embodiment, the transducers are arranged in a circular arrangement around an ultrasound imaging system positioned near a center of the housing.

In another embodiment, the housing is constructed with a rapid-prototyping method.

An ultrasound system is provided, comprising a rapid-prototyping transducer housing, and a plurality of substantially flat, single-element transducers supported by the rapid-prototyping transducer housing, the transducers being physically separated from another by the rapid-prototyping transducer housing and arranged on the rapid-prototyping transducer housing so as to share a common focal point, the plurality of transducers being configured to apply ultrasound energy to the focal point.

A method of designing and manufacturing an ultrasound system is also provided, comprising designing a transducer housing shell to a desired geometry in a 3D computer aided design software, and constructing the transducer housing shell using a rapid-prototyping method.

In some embodiments, the designing step further comprises designing the transducer housing shell to a desired geometry so that a plurality of openings in the housing shell are aligned to converge upon a common focal point.

In another embodiment, the method further comprises inserting a plurality of substantially flat, unfocused piezoelectric or piezoceramic elements into the transducer housing shell so that ultrasound energy from the piezoelectric or piezoceramic elements converges upon a common focal point.

In some embodiments, the method further comprises inserting a plurality of curved, unfocused piezoelectric or piezoceramic elements into the transducer housing shell so that ultrasound energy from the piezoelectric or piezoceramic elements converges upon a common focal point.

In some embodiments, the method further comprises constructing a plurality of transducer element modules with the rapid-prototyping method, and inserting the transducer element modules into the openings of the transducer housing shell.

In one embodiment, the rapid-prototyping method is selected from the group consisting of fused-deposition modeling, 3D printing, and stereolithography.

In another embodiment, the method comprises designing a plurality of acoustic focusing lenses into the housing in the 3D computer aided design software, and constructing the acoustic focusing lenses using the rapid-prototyping method.

In some embodiments, the plurality of acoustic focusing lenses are integral to the transducer housing shell.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1C are illustrations of rapid-prototyping methods utilized for transducer manufacture.

FIGS. 3A-3B illustrate transducers produced using a multi-element spherical shell method with rapid prototyped housing.

FIGS. 4A-4F illustrate a transducer constructed by a rapid-prototyped molding method.

FIGS. 8A-8B illustrate a schematic of a modular element hemispherical transducer housing shell populated with multiple single element housing modules.

FIGS. 12A-12F illustrate impedance traces of elements without (top) and with (bottom) a matching layer/lens. The element impedance is shown directly connected to the element terminals (left), at the end of a 2-meter cable attached to the elements (center), and at the input to the voltage gain network (right).

FIGS. 14A-14F illustrates equivalent surface pressure in the load for an element without (top) and with (bottom) matching layer and lens at 3 separate frequencies. The matching layer/lens element shows faster ringup time and more consistent pressure output across the bandwidth.

FIGS. 15A-15D illustrate impulse response of transducer elements without (top) and with (bottom) a matching layer. The voltage response (left) and pressure response (right) are shown.

FIGS. 16A-16D illustrate voltage (left) and pressure (right) for matched and unmatched elements at their maximum output frequency (860 kHz).

DETAILED DESCRIPTION

Figure 2B:
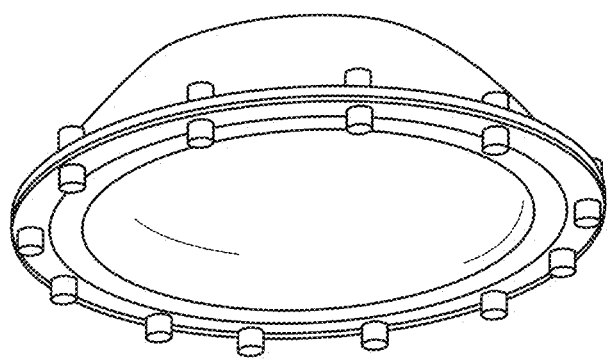
FIGS. 2A-2B illustrate transducer embodiments designed using a single piezoelectric element with rapid prototyped housing method. Housing provides waterproofing for internal connections and mounting hardware.

This disclosure describes novel rapid-prototyping methods and designs and manufacturing methods for ultrasound transducers. The transducers can be made of multiple flat (unfocused) or high f-number (less curved) piezoelectric or piezoceramic elements in a housing shell built from rapid-prototyping, with acoustic focusing lens, matching layer, and mechanical and electric isolation all incorporated in the housing shell. The focusing of the transducer can be achieved by application of appropriately designed acoustic lens to each element, which can be part of the housing shell or separate components that are assembled into the housing shell. The housing shell can have the appropriate geometry to align all the elements to achieve a desired focal pattern. The acoustic lens and housing shell can be made into any arbitrary geometry and dimension. They can first be designed in a 3D computer aided design (CAD) software such as SolidWorks, TurboCAD, Autodesk Inventor, and then constructed through rapid-prototyping. Examples will be given to design and manufacture high pressure, focused ultrasound transducers using this method, particularly for histotripsy applications. The rapid-prototyping method has the following advantages in comparison to the current transducer construction methods using subtractive (e.g. machining) or formative (e.g. injection molding):

Rapid-prototyping method and designs can significantly reduce construction cost of a large aperture, lower f-number (more curved, f-number=focal distance/transducer aperture diameter) ultrasound transducer. Conventional transducer construction methods typically utilize expensive large piece spherically curved ceramic segments. In comparison, rapid-prototyping methods described herein utilize inexpensive small flat or less curved elements. Using these methods, the cost to construct a larger aperture, lower f-number transducer can be reduced for more than an order of magnitude in comparison to the cost for an equivalent transducer made using one large piece crystal.

Rapid-prototyping method and designs can significantly reduce the construction time and accelerate design iterations. Conventional manufacturing of a large aperture curved crystal transducers with high precision is a long, complex procedure requiring highly specialized expertise and equipment. Usually it takes 6 weeks-6 months to obtain a transducer from a commercial company due to the lengthy manufacturing procedure. In comparison, it takes about a few days to assemble a large aperture low f-number transducer using rapid-prototyping transducer if access to a rapid-prototyping machine is available. Particularly for developing a new device where multiple design iterations are required, the device development process can be substantially accelerated.

Rapid-prototyping allows complex shapes that cannot be produced with subtractive or formative methods. For specific clinical applications, a complex shape aperture may be desired to either fit a particular acoustic window or to obtain a particular focal pattern. Using a rapid-prototyping method, any arbitrary geometry can be designed and constructed, which is not possible with existing subtractive (e.g., machining) or formative (e.g., injection molding) methods.

Rapid-prototyping methods can be used both for building single focused transducers and array transducers (such as annular array or phased array). Construction of the array can utilize multiple decoupled elements that can be mechanically and electronically isolated.

Rapid-prototyping designs and methods can incorporate acoustic matching layer(s) configured to significantly improved bandwidth and amplitude output. To improve the transducer bandwidth and amplitude output, a thin layer (generally ¼ wavelength) of material with the appropriate acoustic impedance can be placed between the curved piezoelectric crystal and the front surface of the transducer. Traditionally, applying a uniform thickness sub-millimeter layer material such as an epoxy mixture to the curved crystal is technically very challenging, and how it is done is generally guarded as a trade secret for transducer manufacturing companies. In comparison, using a rapid-prototyping method, application of the acoustic layer can be achieved relatively easy by incorporating small offsetting pads between the crystal and the front housing surface in the AutoCAD design. The desired thickness offsetting pads allow a crystal to be placed at a precise distance from a front housing surface. A metal filled epoxy, which can have the appropriate acoustic impedance for the acoustic matching layer, can be injected into the space surrounded by the offsetting pads before placing the crystal. The epoxy mixture can then be used to bond the element to the housing and provide the proper matching layer thickness and acoustic impedance. The front housing surface of SLA material can act as a second acoustic matching layer for further improvement in output.

For maximum acoustic output, a typical ultrasound transducer has one face of the crystal in mechanical contact with the propagation medium (usually with intervening matching layers) while the back face is mechanically isolated by a very low impedance medium (usually air or a low density foam). Rapid-prototyping enables designs in which the fixture or housing for the crystal incorporates these isolation and propagation features.

In addition to mechanical isolation, the faces of the crystal must be electrically isolated from each other as the difference in electrical potential applied is the source of the acoustic output. The rapid prototype fixture or housing can be constructed of an insulator material to provide this electrical isolation.

A rapid prototype transducer fixture or housing can incorporate electrical contacts that improve reliability and simplify assembly. Electrical contact in a conventional ultrasound transducer is often made by soldering wires to electrodes on the faces of the crystal. Application of these solder connections generally cannot be automated requiring a skilled technician for the assembly process and are prone to mechanical failure over time during operation of the transducer. Spring loaded pin or leaf electrical contacts can be easily incorporated into the housing allowing for easier assembly.

In designs that apply rapid-prototyping, an acoustic lens can be used to achieve focusing and can be made of specific materials with low acoustic attenuation and high sound speed relative to water and materials with mechanical properties that can construct thin lens. This allows transmission most of the sound energy from the transducer to the load and construction of a high precision focusing acoustic lens. An acoustic lens can also be made using machining. However, machined complex lens structures cannot be produced to achieve a particular focal pattern at the same cost/time as rapid-prototyping.

Rapid-prototyping can also be used to build housing shells for single piece large curved crystal or multiple curved crystals for transducer construction.

This disclosure describes designs and construction methodologies for producing high-pressure pulsed output focused therapy transducers by rapid-prototyping. The transducer is designed to maximize transducer bandwidth and instantaneous pressure output rather than highest average intensity output. Rapid-prototyping is employed to create acoustic lens, features for acoustic matching layers, and housings for piezoceramic elements. Rapid-prototyping materials are acoustically characterized to determine their transmissive properties for acoustic lens. Composite matching layers can be formulated and characterized to allow large transducer bandwidth and high pressure output. A version of the 1-D piezoelectric KLM model is developed and combined with a propagation model to determine the expected output from therapy elements. Matching and unmatched ceramic elements are tested for mechanical and thermal failure modes and limits to compare their output potential. Several multi-element transducers are constructed and characterized for pressure output, element alignment, and element impedance.

This disclosure can describe therapy systems that use Histotripsy therapy to generate lesions through rib or bone aberrators without applying any correction mechanisms other than transducer power modulation to compensate for attenuation effects. The ultrasound therapy systems can be configured to generate Histotripsy pulses to deliver Histotripsy therapy to tissue. Histotripsy uses controlled cavitation bubble clouds to induce mechanical tissue fractionation. Histotripsy bubble clouds can be produced by delivering Histotripsy energy to tissue with a Histotripsy transducer, defined by using short (<20 nsec), high pressure (peak negative pressure >10 MPa) shockwave ultrasound pulses at a low duty cycle, typically <5%, minimizing thermal effects. Based on the high echogenicity of cavitating bubble clouds, treatment can also be readily monitored in real time using any conventional ultrasound imaging system, allowing the operator to acknowledge whether cavitation bubble clouds have been generated.

The tissue fractionation effect from Histotripsy therapy occurs when the focal pressure exceeds a certain threshold level at which a cavitation bubble cloud is initiated. Based on this threshold mechanism, Histotripsy therapy can be controlled to generate precise lesions through the ribs or bone provided that the pressure main beam maintains its shape and is above the bubble cloud initiation threshold while secondary lobes resulting from the bone aerator remain below the threshold and thus do not initiate a cavitation bubble cloud.

Figure 2A:
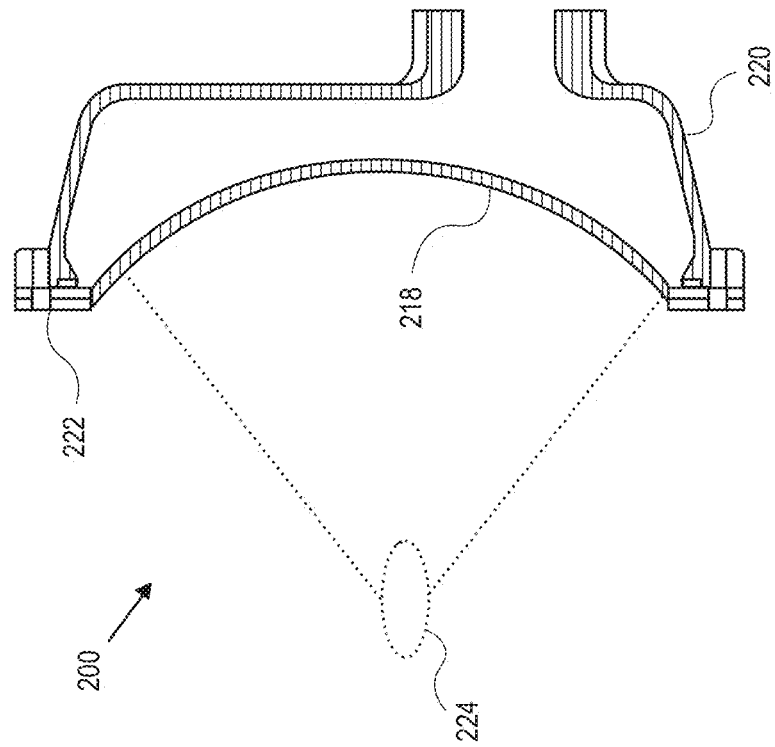

Ultrasound therapy system can be designed and produced in several forms with rapid-prototyping:

FIGS. 2A and 2B show two embodiments of an ultrasound therapy system. FIG. 2A is a cross-sectional view of an ultrasound therapy system 200 having a piezoelectric transducer element 218 that is cut or split up into a plurality of individual transducer elements. The plurality of transducer elements can be arranged to achieve the curved or concave shape shown in FIG. 2A. The transducer element 218 can be held in a rapid-prototyping housing 220 with a plurality of element retaining rings 222. The element 218 can be configured to direct ultrasound energy to a focal zone 224. FIG. 2B is a photograph of a similar therapy system, however in this embodiment the transducer is made up of a single transducer element that has been specially manufactured to achieve the curved shape. In some embodiments, the transducers of these embodiments can be driven at 750 kHz and have an aperture of up to 15 cm with a focal length of up to 10 cm. The transducer design of FIG. 2B uses a single, solid, spherical segment of piezoceramic material. The element can be sealed into a housing 220 constructed on a rapid-prototyping machine, with the concave side of the transducer in contact with the load medium (ultrasound medium that couples the transducer with the target). This is the simplest and most time-efficient method of construction.

As described above, the transducer design of FIG. 2A can be constructed using a single, solid, spherical segment of piezoceramic material which has been electrically separated on one electrode into multiple sub-elements. The ceramic can be sealed into a housing constructed on a rapid-prototyping machine, with the concave side of the transducer in contact with the load medium. This method is more time-consuming than the embodiment of FIG. 2B, because each element requires cabling and driving individually. However, small elements have a higher impedance than one equivalent large element, and can be driven to higher voltage for a given amplifier system with appropriate electrical networks.

FIG. 3A illustrates a cross-sectional view of one embodiment of a rapid-prototyping ultrasound therapy system 300 that includes a rapid-prototyping housing 320 and a plurality of spherical piezoelectric transducer elements 318. In some embodiments, the transducer elements can be can be substantially flat, single-element transducer elements. For example, each transducer element 318 in FIGS. 3A-3B can be a single transducer element, formed from a single sheet or piece of piezoelectric material. Constructing the therapy system with a plurality of flat single-element transducers can significantly reduce costs and construction time of ultrasound therapy systems.

The housing 320 can be fabricated by rapid-prototyping with a housing design in which the transducer elements 318 are precisely aligned towards common focal point 324. As shown, the housing comprises a generally concave or "bowl-shaped" design which allows the transducer elements to share a common focal point. The transducer elements 318 can each be sealed into the housing, with the transducers in contact with a load medium. The housing 320 can also include electrode wire ports 326 to facilitate electrical connection to the elements 318. A central hole or port 328 in the housing can allow for an ultrasound imaging system to be placed for targeting and feedback during treatment. FIG. 3B is a photograph of the transducer 300 of FIG. 3A. In the example of FIG. 3B, the rapid-prototyping ultrasound transducer can include eight spherical transducer elements disposed around the central port. Each of the transducer elements can be secured within the housing so as to be aligned towards the same focal point.

In some embodiments, the transducer elements 318 of FIGS. 3A and 3B can be other shapes, or can even be curved to match or approach the curvature of the housing itself. For example, the transducer elements can be square, rectangular, oval, polygonal, concave, convex, etc.

One of the most difficult aspects of making multi-element focused transducers or arrays is ensuring alignment of elements. This can be easily accomplished with the rapid-prototyping methods described herein. For example, the system of FIGS. 3A-3B utilizes a precisely designed housing configured to position a plurality of flat transducer elements so they share a common focal point. This design is beneficial because smaller ceramics are more available than large single ceramics commercially.

In another embodiment, illustrated by FIGS. 4A-4F, a rapid-prototyping ultrasound transducer 400 can be constructed by aligning multiple spherical transducer elements 418 of piezoceramic material, all of them aligned confocally by placement on a rapid-prototyped mold face 430, back-filling the elements with a solidifying material, such as a rigid polyurethane foam, and constructing a housing around the material. The mold face can then be removed after solidification of the back-fill, leaving the elements in contact with the load medium. This design and method allows use of non-rapid-prototyping materials for the actual housing, but has the benefit of using rapid-prototyping for precise alignment of elements. FIGS. 4A-4D show front, side, top, and axonometric views of a mold 430 for aligning transducer elements 418 in a rapid-prototyping ultrasound transducer. FIGS. 4E and 4F are photographs of the mold and completed transducer, respectively. In the examples of FIGS. 4A-4F, one particular rapid-prototyping mold can be configured to align, for example, 19 transducer elements.

Figure 5C:
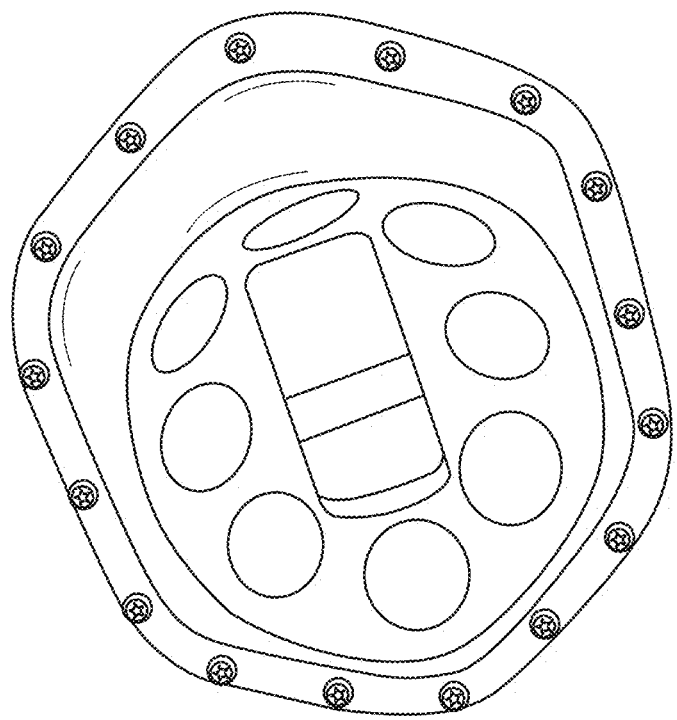
FIGS. 5A-5C illustrate a multi-element transducer constructed by a matching layer and acoustic lens method.
Figure 5A:
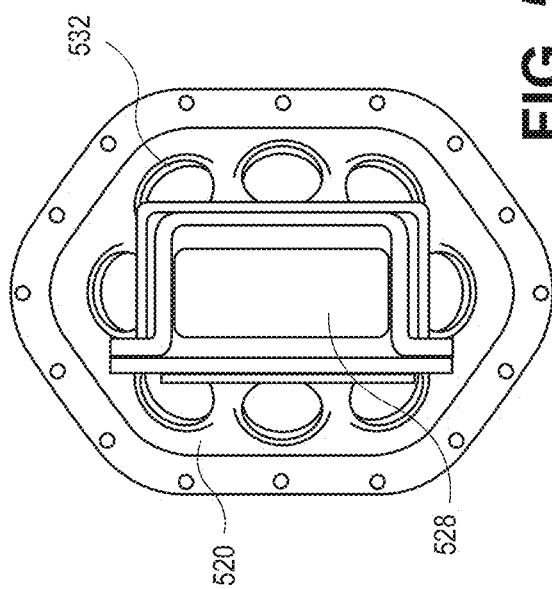
Figure 5B:
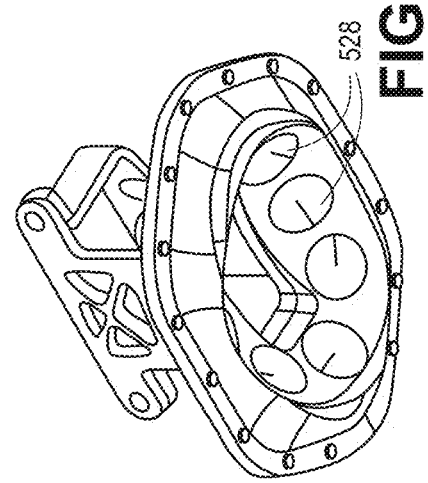

FIGS. 5A-5C illustrate one embodiment of a rapid-prototyping ultrasound transducer 500 configured for treatment of thrombolysis. FIGS. 5A and 5B show top and axonometric views of the transducer, and FIG. 5C is a picture of a completed transducer. This particular transducer design can use a single or multiple flat transducer elements of piezoceramic material positioned with the elements facing normal to the direction of the transducer focus. The transducer 500 can further include acoustic lenses 532 applied to focus the output of the transducer elements to the transducer focus. In this design, a rapid-prototyping machine generates a housing 520 including the acoustic lenses for the individual focused transducer elements. The acoustic lenses are integral to the housing and thus the housing and lenses can be constructed with a material that optimizes and transmits ultrasound waves. This requires specific rapid-prototyped materials, described below, which permit ultrasound transmission. This embodiment can further include a central hole or port 528 in the housing can allow for an ultrasound imaging system to be placed for targeting and feedback during treatment.

In some embodiments, one or more matching layers may be applied between each transducer element and acoustic lens. If a matching layer is not applied, the transducer element can be directly adhered to the back of the lens. If a matching layer is applied, standoffs can be either included in the rapid prototyped construct or added secondarily into the element space to create a gap between the transducer element and the acoustic lens to be filled with the matching layer material.

Figure 6B:
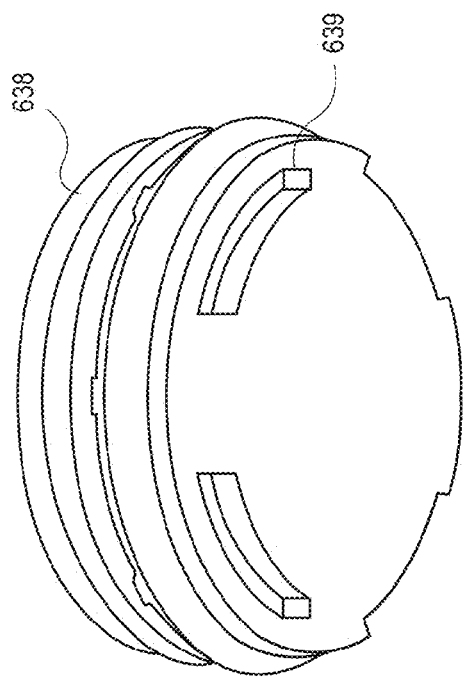
FIG. 6A-6D illustrate a design of a single element housing module with standoffs to allow accurate matching layer application.
Figure 6D:
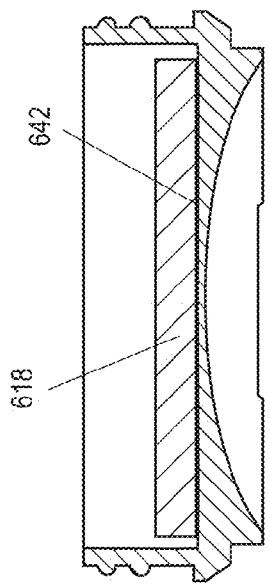
Figure 6A:
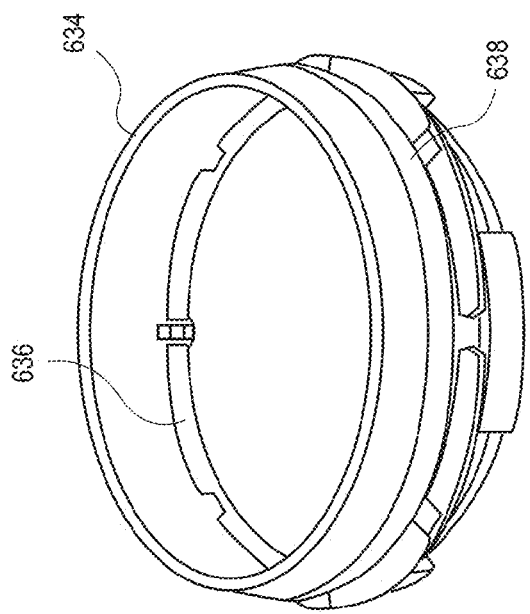

FIGS. 6A-6D illustrate a transducer element housing module with standoffs to allow for accurate matching layer application. In FIG. 6A, a transducer element module 634 can include matching layer overflow slits 636 and housing threads 638 configured to allow the transducer element module 634 to be screwed into a larger, complex rapid-prototyping housing (such housing 320 in FIGS. 3A-3B). In other embodiments, the transducer element modules can be "snapped" into place in the housing, or held in place with other features of the housing such as clips, slide-locks, pressure-fittings, wedge-fittings, or the like. In FIG. 6B, the transducer element module 634 can include indentations or protruding features 639 configured to engage a socket tool, for ease of installing or screwing the module into the larger therapy housing.

Figure 6C:
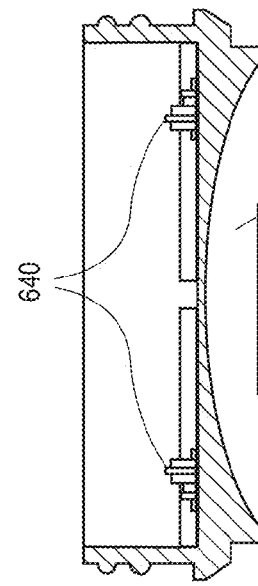

FIG. 6C is a cross-sectional view of the transducer element module 634 and shows matching layer standoffs 640 and acoustic lenses 632. In FIG. 6C, multiple standoffs are shown in a variety of heights and thicknesses. It should be understood that in use, only a single pair of matching layer standoffs are needed to create a matching layer. The standoffs allow for accurate matching layer application between each lens and transducer element, by creating a space for the matching layer between a front surface of the transducer element and a rear surface of the acoustic lens. Referring to FIGS. 6A and 6C, a matching layer can be applied to the module so as to fill the space defined by the matching layer standoffs 640. If excess matching layer material is applied, the overflow slits 636 can allow excess matching layer material to flow out of the module so that the matching layer material does not extend beyond the matching layer standoffs.

FIG. 6D shows a cross-sectional view of the transducer element housing 634 with the transducer element 618 and matching layer 642 in place in the housing 634. The matching layer then acts as the adhering compound between the transducer element and the lens and acoustically couples the transducer to the lens. In some embodiments, more complex tapered matching layers can be built into the acoustic lens using rapid-prototyping without additional time or cost required see below), which would be difficult to achieve with machining.

Figure 7:
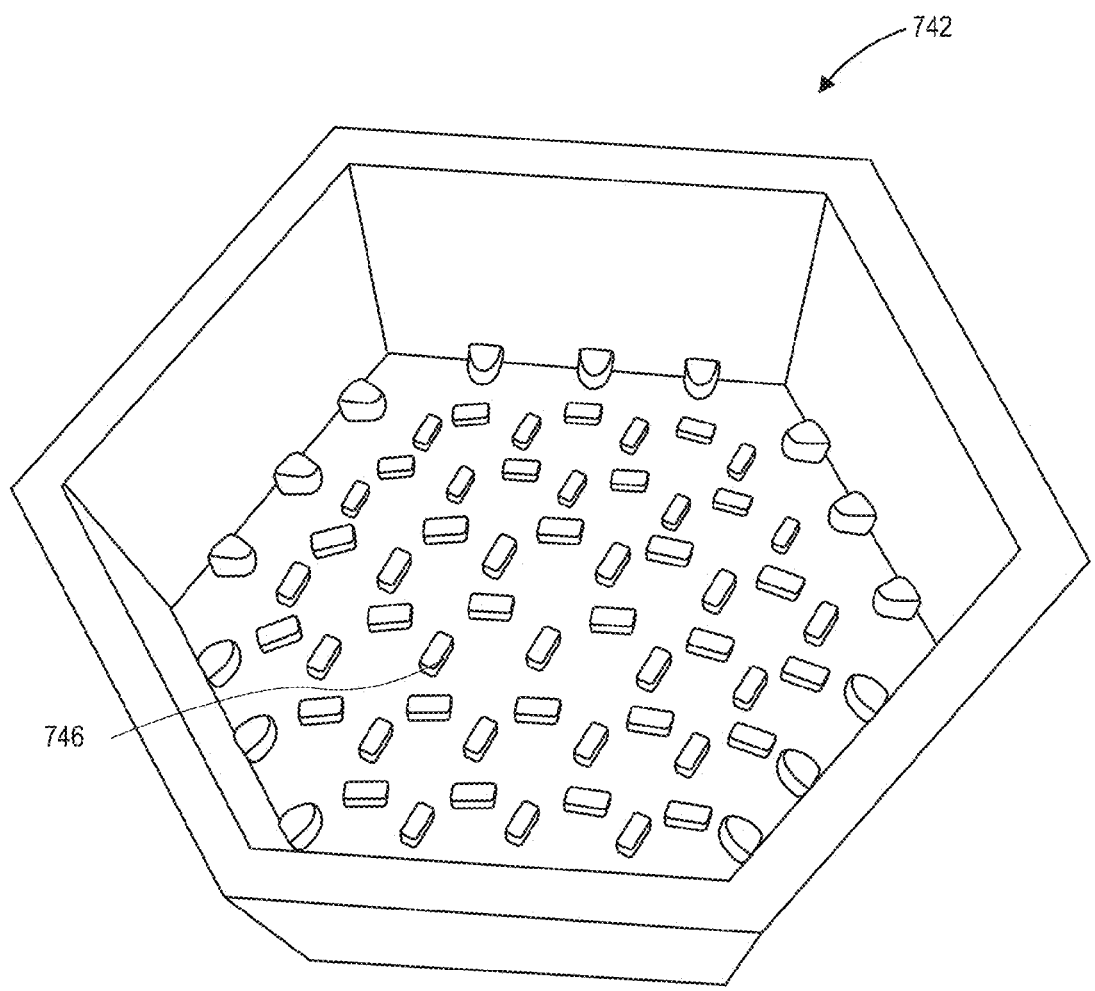
FIG. 7 illustrates a model for a 37 element phased-array showing alignment features (posts) and matching layer defining features built into the same structure defining the transducer housing. This structure could be scaled to hundreds or thousands of elements and built by a rapid-prototyping machine.

Rapid-prototyping can be particularly advantageous for the construction of phased-array transducer designs. An electronically steerable array requires hundreds to thousands of very small elements arranged over a curved surface with precision alignment. Rapid-prototyping allows the thousands of fine alignment features required to be constructed on a single scaffold frame or shell holding the elements such as is shown by frame 744 in FIG. 7. In this particular embodiment, the frame 744 can include alignment features 746 and matching layer defining features built into the frame. This particular embodiment is a model for a 37 element phased-array transducer, but can be scaled to hundreds or even thousands of elements and be built by a rapid-prototyping machine. Furthermore, electrical contacts can be a spring loaded pin or leaf contacts greatly simplifying assembly.

A transducer design can be constructed using modular transducer element housings (such as the transducer element housings 634 of FIG. 6), which can be confocally mounted in a larger scaffolding shell or housing that contains threaded sockets. FIG. 8A illustrates a rapid-prototyping housing 820 filled with a plurality of modular transducer element housings 834. Each element housing can be a self-contained acoustic lens module made with rapid-prototyping material to which a flat piezoceramic disk can be mated. In the example shown in FIG. 8B, the transducer housings 834 can have external threaded walls 838 that connect each individual transducer element housing to the matching sockets in the housing 820. A silicone adhesive can be applied to the threads to make the threading junction waterproof while still allowing later removal of the element housing from the shell if necessary.

Figure 9A:
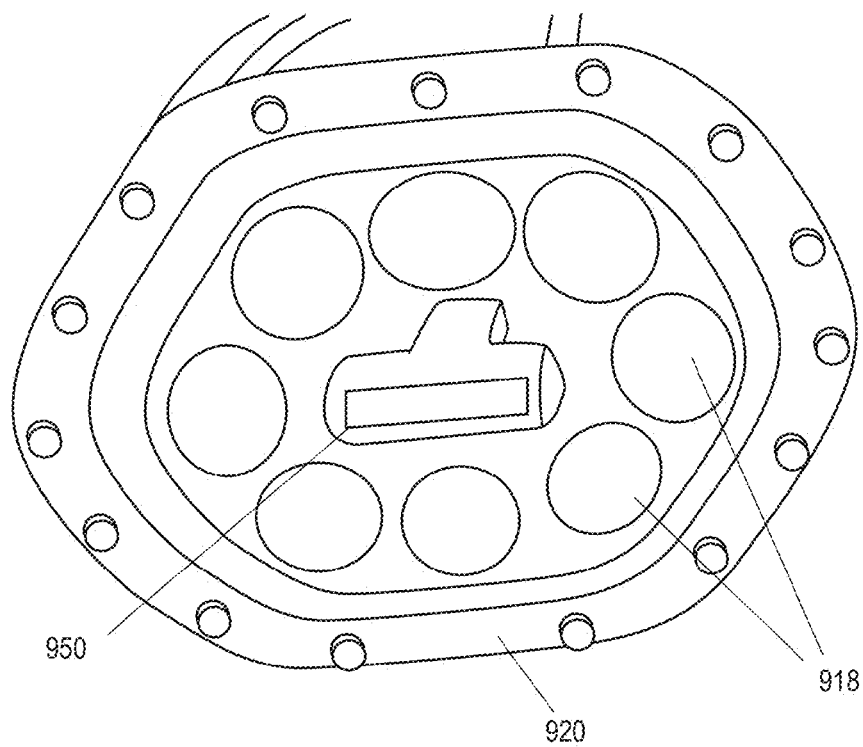
FIGS. 9A-9B illustrate an imaging probe holder alignment incorporated into the transducer housing shell using rapid-prototyping.
Figure 9B:
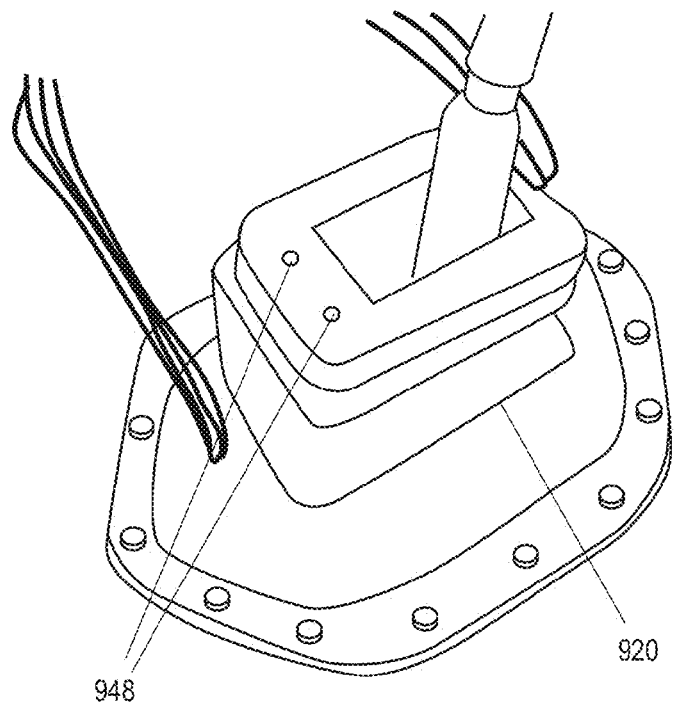

In designs where another device needs to be aligned with the rapid-prototyping transducer, an alignment structure can be incorporated easily into the housing built using rapid-prototyping. FIGS. 9A-9B show an imaging probe holder 948 incorporated into a housing 920 to allow precise alignment between an imaging system 950 and the transducer elements 918 of transducer 900. The imaging system can be positioned between the imaging probe holder, which can be molded to the housing geometry. The housing can then clamp the holder together when the imaging system is in place.

In some embodiments, a cavitation monitoring device can also be aligned with the therapy transducer by incorporating such alignment structure. In another embodiment, optical fibers or laser pointers can be incorporated into the housing 920 where an intersection of the laser beams or optical fibers is configured to be aligned with the focus of the transducer elements to visualize the focus.

To construct a large transducer that may either exceed the dimension limit of the available rapid-prototyping machine, it is possible to design several sectors of the housing shell with locking mechanism that can assemble to a larger transducer while maintaining the alignment of the elements on separate sectors. For example, a large spherical segment transducer built with multiple flat elements can be assembled by pizza slice sub-aperture with locking mechanism to connect the various sectors of the housing shell.

To maximize the use of surface area, elements of shapes other than circular shape can be used. For example, square, rectangular, and hexagon can be used maximize the usage of surface area and is particularly helpful in constructing compact transducers with high pressure output. Such transducers can be built with acoustic lens and matching layer following the same procedures as described earlier using the circular flat elements.

Construction of Focused Transducer Using Flat Elements and Acoustic Lens

The advantages of the design and construction methods described above, over the others are: (1) flat ceramics (for the transducer elements) can be used, which are more readily available than curved ceramics, significantly reducing the cost and time for transducer construction, (2) matching layers can be applied easily, allowing much higher surface pressure output, (3) alignment of multiple elements is more easily achieved with lens and flat elements than spherically-focused elements, and (4) electrodes do not contact the load medium, meaning the transducer is well isolated from the patient. The disadvantages of this design are (1) lower heat dissipation and achievable average power output and (2) there is some attenuation due to matching layer/lens. This design is particularly useful for transducers with low focusing gain, where high surface pressure may be needed to generate adequate focal pressure.

Using acoustic lens with flat elements, the focusing of sound requires that the lens geometry is shaped differently than from a spherical curvature. For a plane wave propagating in the lens medium, the surface must be concave for $c_{lens} > c_{load}$. In this case, it is ideal that the surface is elliptical. This shape is difficult to produce in subtractive machining without the use of computer numerical control (CNC), but can be accomplished using rapid-prototyping with the same time and difficulty as producing a spherical curvature. However, it is necessary that the material has sufficiently low attenuation and high sound speed and that the lens can be made thin and transmit most of the sound energy to the load.

Matching layers can be applied to maximize the bandwidth of imaging transducers and maximize power transfer in HIFU transducers. In these systems, the matching layer impedance is often chosen to be near the geometric mean between the element and load medium. While this does optimize the bandwidth, theoretical treatment shows, in fact, that the power transfer at a particular frequency in the bandwidth is lowered compared to the unmatched case. The matching layer acts to dampen the resonance of the transducer, but at the same time, attenuates some of the energy transferred. For histotripsy, efficiency is not the key parameter, but rather, maximum pressure output for short pulse duration. Broadband matching facilitates this by providing several advantages over unmatched elements.

Matching layers allow a greater percentage transfer of energy per cycle from the element into the medium. For instance, in unmatched elements, the peak pressure in water relative to the peak pressure in a resonant PZT ceramic is about 0.08. In a matched element, this ratio is about 0.22. This means that the same pressure in water can be achieved with lower stress on the element. Since PZT has an ultimate stress limit prior to fracture, the pressure output into the water below this ultimate limit is higher with matching.

Matching layers can increase the bandwidth of the transducer. This is important in histotripsy where short duration pulses (2-10 cycles) are required to prevent heating the medium and to maximize cavitation activity. Higher bandwidth can alternatively be achieved by electrical tuning of the elements. This higher bandwidth provides a method for testing variation of transducer driving frequency and its effect on histotripsy as well.

Matching layers can increase the electrical impedance of a transducer element. This means a lower current draw is needed from the amplifier for a given voltage, and less 'electric stress' is placed on the driving system. However, this usually comes at the cost of a reduced output to some extent. Thus, a voltage gain matching network is applied to generate a greater voltage across the elements.

In the case where the matching layer is not a conductive material, the matching layer provides a means of electrical isolation from the load medium and the patient. When acoustic lens are made from rapid-prototyping material, this is usually not an issue because most rapid-prototyping polymers are insulators.

Histotripsy Transducer Design and Fabrication Process

To design therapy or histotripsy transducers according to the embodiments described above, the transducer specifications can be determined for a transducer based on the specific clinical application. For example, transducer aperture size is determined by the available acoustic window size. The focal distance of the transducer is determined by the thickness of the intervening tissue. The focal zone size, which primarily depends on the transducer frequency and f-number, is selected by the requisite treatment volume and precision requirements.

Second, based on these design requirements, the selection and geometric arrangements of individual elements can be determined by iterative simulation with piezoelectrical and propagation models to find appropriate element geometry, quantity, and arrangement.

Third, element quantity and arrangement can be chosen according to the transducer specifications. A propagation model can be employed to evaluate the transducer focal gain and focal dimensions. Using the output from the Krimholtz, Leedom, and Matthaei (KLM) model as the input for this model, some idea of the focal pressure can be obtained. After the element geometric configuration is chosen within the transducer specifications, the transducer housing can be designed in a CAD program. The design files can then be used to control automated rapid-prototype fabrication of the housing. After the ceramic elements and cabling are sealed into the housing, the constructed transducer can then be characterized for focal pressure, beam profile, and cavitation activity and compared with the specified values.

An example of the design and construction of a transducer for application to treating deep-vein thrombosis (and also illustrated in FIGS. 5A-5B) in the femoral veins with histotripsy is described in the following sections. The transducer incorporated a linear array ultrasound imager to optimize the therapy feedback imaging. The focal volume of the transducer was specified such that cavitation would be generated solely within the target vessel lumen to minimize undesired collateral damage. An integral transducer housing that incorporates multiple acoustic lenses, standoff features for acoustic matching layers, and housings for multiple piezoceramic elements was designed and easily fabricated using rapid-prototyping. Rapid-prototyping materials were acoustically characterized to determine their transmissive properties for the acoustic lens. Composite matching layers, which included the lens and matching layer adhesive materials were formulated and characterized to allow large transducer bandwidth and high pressure output. Matched and unmatched ceramic elements were tested for mechanical failure modes and limits to compare their output potential. The transducers were constructed and characterized for pressure output, element alignment accuracy, and electrical impedance.

Characterization of Materials for Transducer Design

Materials for the piezoceramic elements, matching layer, and acoustic lens were characterized. The sound speed and attenuation of rapid-prototyped polymers was evaluated to optimize the acoustic properties of the acoustic lens. A suitable material for the matching layer was also identified and formulated. Finally, the mechanical strength of several piezoceramic materials was considered to determine the maximum voltage which could be applied to the elements. The methods and results for testing of these materials are included in this section.

Characterization of Rapid-Prototyping Materials

Several methods of rapid-prototyping were evaluated by testing the acoustic properties of material samples fabricated using fused-deposition modeling (FDM), 3D printing, and stereolithography apparatus (SLA). These three processes are illustrated in FIGS. 1A-1C. Referring to FIG. 1A, an FDM machine 100a operates by applying a melted thermoplastic 102 through a nozzle 104, which is fed by a solid spool 106 of plastic material. This plastic is dispensed onto a CNC platform 108 and solidifies in place. The pieces produced by an FDM machine can be made with the highest material density settings on the machine to ensure low porosity.

Referring to FIG. 1B, a 3D printer can dispense photopolymer drops with a computer controlled nozzle 102 and cure the photopolymer with, for example, UV lamps or UV lasers 110 immediately after application onto the previous solid layer. In some embodiments, the lateral print resolution is 100 µm and the vertical build layer step resolution is 16 µm. Different photopolymers can be placed to form a composite material with the rigidity varying between soft rubber to hard plastic. For the purposes of generating specified acoustic parts, only the hard plastic material was tested because softer materials would not maintain precisely formed shapes. In some embodiments, the 3D printer uses a steerable focused UV laser to cure selected regions in a bath of a liquid photopolymer. Some systems can have a lateral resolution of about 75 µm and vertical step size of 100 µm. Several material types were tested from a 3D printing machine such as this.

FIG. 1C illustrates a stereolithography apparatus (SLA) 100c which uses a focused, steerable UV laser 112 to cure select regions of photopolymer on the surface of a liquid bath 114. After each layer is constructed, an elevator 116 can drop the cured material into the bath so the next layer can be formed.

Density of a material can be measured directly from the known volume of the part and the mass. A transmission method was used to measure the sound speed and attenuation. Two flat, circular PZT transducers with 1 cm diameter were positioned 8 cm apart, and the material was positioned within 5 mm of the receiver. One transducer was connected to a function generator driven with a short burst at 1 MHz. The other transducer was used as a received, attached to a digital storage oscilloscope. This method allowed near plane wave propagation through the material. The sound speed was determined from the cross-correlation of two waveforms, one received in open water and the other with the material in the acoustic path. The sound speed can be found from the time $\Delta t$ between the signals from:

$$c_t = \frac{c_w x_t}{c_w \Delta t + x_t}, \tag{1}$$

where $x_t$ is the material thickness and $c_w$ is the sound speed in water. With this information, the acoustic impedance is calculated from the product of the sound speed and density. Finally, the attenuation is calculated from the relative amplitude with and without the material in the path, adjusting for the reflections caused by the material/water interfaces calculated with the measured acoustic impedance.

The results are summarized in Table I. ABS plastic printed by an FDM machine displayed slightly lower sound speed and density to molded ABS, but higher attenuation. The density of the printed ABS material with the highest density setting on the system was 93% of that of cast ABS material. While this difference is small, it suggests that air is introduced in the plastic structure during the fabrication process, making the part slightly porous. The result of this added porosity is increased acoustic attenuation, which is undesirable for transmission of sound. Similarly, the material printed by the 3D printer had considerable attenuation of 3 dB/cm at 1 MHz, but a higher sound speed compared with the ABS from the FDM machine.

The SLA materials had acoustic properties consistent with extruded or cast engineering plastics. The sound speed of various samples ranged from 2300-3090 m/s, with a consistent density around 1200 kg/m³ among most samples. While it is desirable to use a material with high sound speed for the acoustic lens to minimize its thickness and attenuation, poor finish quality and limited availability of the materials with highest sound speed precluded their use for transducer construction. The Accura 60 material was chosen to produce most transducer prototypes. Accura 60 is also semi-transparent, which allows identification of printing defects and water infiltration into the housing.

TABLE I

Acoustic properties of rapid prototyped materials and typical plastics.

|  | Material | Density (kg/m3) | Sound Speed (m/s) | Acoustic impedance (MRayl) | Attenuation (dB/cm @ 1 MHz) |
|---|---|---|---|---|---|
| FDM | ABS | 990 | 2040 | 2.02 | 3.5 |
| 3D Printer | Vero White | 1170 | 2370 | 2.77 | 3.0 |
| SLA | Accura 25 | 1200 | 2300 | 2.76 | 3.6 |
|  | Accura 48HTR | 1200 | 2550 | 3.06 |  |
|  | Accura 60 (Blue) | 1210 | 2570 | 3.11 | 4.1 |
|  | Accura 60 (Red) | 1210 | 2540 | 3.07 |  |
|  | Accura PEAK | 1360 | 2860 | 3.89 |  |
|  | Accura Extreme | 1200 | 2390 | 2.87 |  |
|  | Accura Bluestone | 1780 | 3090 | 5.50 |  |
| Plastics | ABS | 1070 | 2170 | 2.32 | 2.3 |
|  | Acrylic | 1190 | 2750 | 3.27 | 1.3 |
|  | Delrin | 1420 | 2430 | 3.45 | 6.0 |
|  | HDPE | 945 | 2221 | 2.10 | 3.0 |
|  | LDPE | 920 | 1950 | 1.79 | 0.5 |
|  | Polypropylene | 890 | 2660 | 2.37 | 3.6 |
|  | Polycarbonate | 1180 | 2270 | 2.68 | 5.0 |
|  | Polystyrene | 1050 | 2400 | 2.52 | 0.4 |
|  | PVC | 1380 | 2380 | 3.28 | 2.2 |

*All plastics attenuation values were recorded at 5 MHz. The values listed for 1 MHz are calculated assuming a linear trend of attenuation vs. frequency Formulation and Characterization of Matching Layers For a piezoceramic element of acoustic impedance $Z_e$ and load impedance $Z_l$, the criteria for a single quarter-wavelength matching layer impedance has been derived by several others. The simplest argument is for transmission of a wave through a simple quarter-wavelength thickness sheet with infinite media on either side. In this case, maximum power transfer is obtained when the matching layer impedance is the geometric mean of the element and load impedances:

$$Z_m = \sqrt{Z_e Z_l} \quad (2)$$

This equation does not account, however, for the finite thickness of the element. Desilets instead formulates the ideal matching layer as if the desired impedance should be achieved at the center-tap of the piezoelectric transmission line within the KLM model, and thus, the front half of the element should be treated as a second matching layer, in addition to the actual matching layer. This results in an alternate formula:

$$Z_m = \sqrt[3]{Z_e Z_l^2} \quad (3)$$

Souquet derived a third equation for the impedance based on the solution that for maximum bandwidth, the transducer mechanical and electrical Q should be equivalent. This leads to a slightly different value for $Z_m$:

$$Z_m = \sqrt[3]{2 Z_e Z_l^2} \quad (4)$$

Note that the goal of the matching layer for the therapy transducers is not necessarily to generate the highest bandwidth, but to increase the element electrical impedance, provide high output at the center frequency, and decrease the stress internal to the element for a given surface pressure. Eq. 4 appears to fulfill these criteria the best, supplying the largest output at the center frequency. However, it has been demonstrated that the addition of a polymer acoustic lens increases the optimal impedance closer to Eq. 2. Thus, for the purposes of design, Eq. 4 is utilized when a matching layer is applied directly between the load and element, while Eq. 2 is applied when an acoustic lens is included.

These experimental results were compared with a theoretical model which predicts sound speed and density of a 0-3 composite material, based on the individual sound speeds and density of components. The modified Reuss model has been shown to be an accurate, simple method for such calculations, where the density is simply defined by the weighted sum of component densities ($\rho$):

$$\rho_c = V_e \rho_e + V_p \rho_p \quad (5)$$

And the sound speed is found from the elastic moduli (M) and volume fractions (V) of the individual components:

$$\frac{1}{M_c} = \frac{V_e}{M_e} + \frac{V_p}{M_p} \quad (6)$$

$$c_c = \sqrt{\frac{M_c}{\rho_c}} \quad (7)$$

These equations were used to determine the matching layer impedance for the experimental mixtures, and compared with the results.

These equations can help determine if such a model can be used in place of experimental tests to find the appropriate formulation for a given piezoceramic type. Matching layer materials were made from epoxy-powder composites. Different formulations of matching layers we created with the chosen types of epoxy and three types of powders. Matching layer test pieces were created by mixing epoxy and powder together, hand stirring the mixture until no dry powder remained in the liquid epoxy. Two epoxies were chosen based on their adhesive capabilities: Hysol E-120HP and TAP Super hard Epoxy. Powders comprised of either silicon carbide (SiC), cerium oxide (CeO$_2$), or tungsten (W), and were mixed in different weight ratios with epoxy. Each mixture was degassed in a vacuum chamber for 20 minutes, then poured into a cylindrical mold to make a cylindrical sample with 2.5 cm diameter and 1 cm thickness. The samples were allowed to cure for 24 hours and then removed from the mold. Each sample's properties were then measured by the same method as the rapid-prototyping materials.

A total of 18 mixtures using cerium (IV) oxide (CeO$_2$), silicon carbide (SiC), or tungsten (W) were used to evaluate the acoustic impedance of the materials as ideal matching layers for transducers with and without lens. Using Eq. 4 for the ideal matching layer without lens, the impedance should be $Z_{ML}$=5.4 MRayl. Using Eq. 2 for the ideal matching layer with lens, the impedance should be $Z_{ML}$=7.0 MRayl.

Figure 10A:
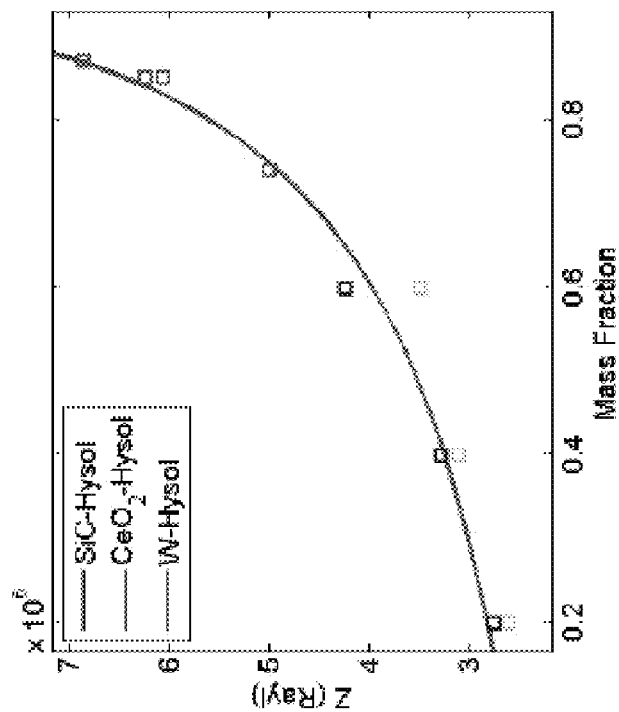
FIGS. 10A-10B illustrate sound speed and acoustic impedance predicted by the model (solid lines) and experimental measurements (squares), all as functions of mass fraction of powder in epoxy. Powders with lower bulk sound speed produced materials with lower sound speed, but impedance vs. fraction was consistent between the three materials, as predicted by the model.
Figure 10B:
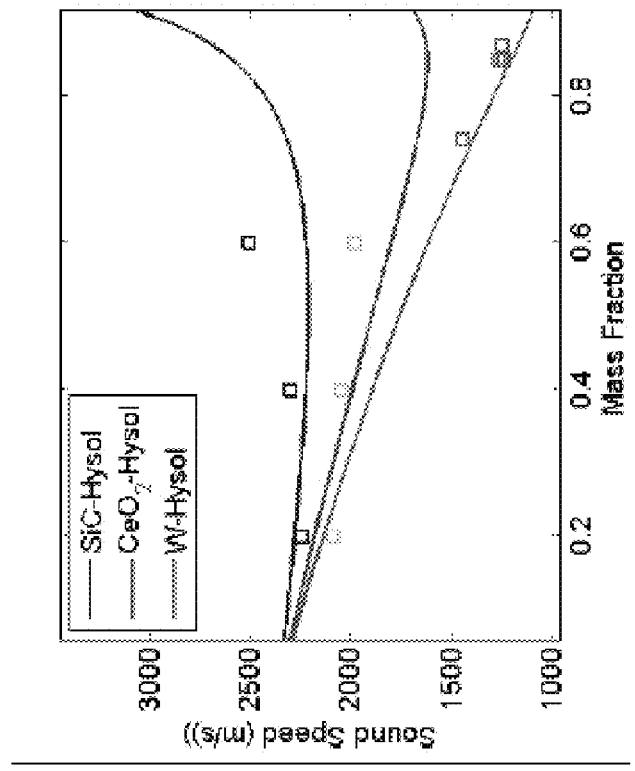

Table II shows the properties of the 18 materials tested with various powders. In general, the sound speed of mixtures first decreases as low fractions of powder are mixed, then rises to the sound speed of the bulk powder material as the fraction approaches 1. However, SiC, which has a very high bulk sound speed of approximately 13000 m/s, showed an increasing trend of the sound speed with powder fraction. This behavior was inconsistent with the model trend, which showed a decrease in apparent sound speed, as shown in FIGS. 10A and 10B. However, all three materials were in good agreement with the calculated acoustic impedance. FIG. 10A shows the sound speed predicted by models with experimental measurements shown by the square data plots, as a function of mass fraction of powder in epoxy. FIG. 10B shows the acoustic impedance predicted by models with experimental measurements shown by the square data plots, as a function of mass fraction of powder in epoxy. Powders with lower bulk sound speed produced materials with lower sound speed, but impedance vs. fraction was consistent between the three materials.

Tungsten proved the most ideal material for use as a matching layer. Due to its high density, a small volume of tungsten was required compared with the other powders, which means the combined mixture was of lower viscosity and more easily degassed. Mixtures of CeO$_2$ and SiC were difficult to mix beyond 60% powder. A mixture of 87% tungsten to Hysol w/w was found to be near the ideal value for a transducer with lens. Mixtures of 78% tungsten to Hysol or 71% tungsten to TAP epoxy were found by the model to produce an appropriate impedance without lens. Attenuation was not recorded for most samples, but for the 87% W/Hysol mixture, the attenuation was 10.5 dB/cm at 1 MHz. For matching layers of quarter-wavelength thickness, the attenuation due to the matching layer would be ~0.4 dB, which gives >95% transmission.

TABLE II

Measured acoustic properties of matching layer mixtures.

| Epoxy Type | Powder Type | Epoxy Fraction (w/w) | Powder Fraction (w/w) | Density (kg/m³) | Sound Speed (m/s) | Acoustic Impedance (MRayl) |
|---|---|---|---|---|---|---|
| TAP | SiC | 0.80 | 0.20 | 1313 | 2608 | 3.42 |
| TAP | SiC | 0.60 | 0.40 | 1483 | 2666 | 3.95 |
| TAP | SiC | 0.40 | 0.60 | 1766 | 2956 | 5.22 |
| TAP | CeO$_2$ | 0.80 | 0.20 | 1335 | 2430 | 3.24 |
| TAP | CeO$_2$ | 0.60 | 0.40 | 1699 | 2356 | 4.00 |
| TAP | CeO$_2$ | 0.40 | 0.60 | 2036 | 2255 | 4.59 |
| TAP | W | 0.60 | 0.40 | 1792 | 1950 | 3.49 |
| TAP | W | 0.40 | 0.60 | 2662 | 1710 | 4.55 |
| TAP | W | 0.15 | 0.85 | 4973 | 1490 | 7.41 |
| Hysol | SiC | 0.80 | 0.20 | 1226 | 2240 | 2.75 |
| Hysol | SiC | 0.60 | 0.40 | 1430 | 2293 | 3.28 |
| Hysol | SiC | 0.40 | 0.60 | 1690 | 2504 | 4.23 |
| Hysol | CeO$_2$ | 0.80 | 0.20 | 1244 | 2081 | 2.59 |
| Hysol | CeO$_2$ | 0.60 | 0.40 | 1519 | 2040 | 3.10 |
| Hysol | CeO$_2$ | 0.40 | 0.60 | 1763 | 1973 | 3.48 |
| Hysol | W | 0.26 | 0.74 | 3462 | 1441 | 4.99 |
| Hysol | W | 0.15 | 0.85 | 4974 | 1253 | 6.23 |
| Hysol | W | 0.15 | 0.85 | 4921 | 1232 | 6.06 |
| Hysol | W | 0.13 | 0.87 | 5527 | 1239 | 6.85 |

Tapered Matching Layers

In order to decrease internal reflections in a transducer, an impedance matching device between the high acoustic impedance transducer material (usually a hard piezoelectric ceramic) and the lower acoustic impedance of water (or high water content tissues) can be employed. Matching layers minimize internal acoustic reflections allowing more energy per cycle to exit the transducer into the target (usually tissue) volume. This also minimizes internal stresses and losses (and resulting high temperatures) inside the transducer ceramic and makes the transducer much more broad-band (thus allowing much shorter ultrasound pulses). Short pulses are essential for some imaging and therapy applications.

One way of making matching layers is to fabricate single (or multiple) discrete layer(s) of materials with impedances between the transducer ceramic (high impedance) and the target volume (usually a high water content tissue, i.e., an impedance close to water). This is a standard way of approaching the problem and the intermediate impedance can often be obtained by using metal powder (e.g., tungsten) loaded epoxy of the appropriate thickness.

An alternative approach which continuously tapers the impedance, or the effective impedance, between that of the high impedance ceramic and that of the low target impedance of tissue (or water) can be accomplished in several ways:

An effective impedance taper can be accomplished by fabricating on the rapid-prototyping polymer surface tapered grooves, cones, or pyramids that are closely spaced at their base. When filled with tungsten-epoxy, or other flowing liquid-like high impedance material (e.g., a low melting temperature metal such as lead or solder-like alloys), a casting is made that starts as virtually 100% high impedance metal or composite epoxy tapering down to 100% prototyping polymer (or air if the cast matching layer is removed from the polymer mold). This casting then looks like a closely packed "bed of nails" if fabricated with cones or pyramids, or a set periodically spaced grooves (either concentric or linear). If the lateral dimensions of the grooves (or cone/pyramids) are much less than a wavelength of the ultrasound, the tapered impedance will approximate a true tapered impedance (such as on could get by using a centrifuge to vary the tungsten powder content in the thickness dimension of the tungsten-epoxy composite before the epoxy sets. The casting would then be bonded directly to the transducer face and when the grooves or valleys are filled with water (no air), a smooth transition between high impedance ceramic and low impedance water is obtained. This approach has the advantage of making the thickness dimension open to any value the designer chooses wherein, with discrete matching layers, this dimension is fixed to some given fraction of a wavelength depending on the design. At higher frequencies, this thickness may so small as to be beyond the precision capabilities of the rapid-prototyping process.

In another embodiment, the grooves, cones, or pyramids of the "tapered-impedance" matching layer structure can be cut, machined, stamped, embossed, or molded into the high impedance matching layer structure. Soft metals, metals softened by high temperature before "imprinting," or epoxy-metal-powder composites imprinted just before the epoxy becomes hard by "setting or curing" are all possible assembly methods. An example of such an approach would be to stack many standard double edge safety razor blades together making a periodic linear groove die that could be used to impress the reverse pattern into a still tacky epoxy-tungsten-powder layer on the transducer surface. The dimensions of such safety razor blades would be ideal for transducers up to several MHz in frequency (nominal double edge safety razor blade thickness is about 0.25 mm or about ⅙ wavelength of one MHz ultrasound (in water)). Exact dimensions are not critical as long as the period of the repeating groove or pyramid pattern is less than a wavelength.

In the above matching layer "tapered" constructs, it is also possible to vary the taper from some linear change over the somewhat arbitrary thickness to other functions, e.g., "exponential" or some other thickness dimension taper profile dictated by some optimization criteria. This latitude in choice of the overall thickness of the tapered components, and the ability to change the mathematical description of the taper contour, are important design advantages over the more standard discrete thickness matching layers. The matching layer efficacy is also significantly improved.

Array Fabrication Consequences of Tapered Matching Layers

The use of micro-tapered constructs (closely spaced grooves, cones, or pyramids) offers a potentially useful way to fabricate transducer and transducer arrays with the 3-D prototyping process. Because the micro-tapered geometry, the length of the tapered constructs is somewhat arbitrary removing the axial dimension of the overall matching layer as a fixed design parameter. Usually, the more gradual the taper, the more effective is the matching and the thicker the matching layer construct. However, increased thickness may increase attenuation, so a trade-off exists.

One possible fabrication method becomes possible with thicker more robust matching layers, namely, the substrate and framework for array element attachment can become the matching layer construct itself, as opposed to a separate fabricated framework. This may significantly simplify overall fabrication wherein the transducer, or fabricated segments of it, would only need mounting in a simplified framework in order to obtain a finished transducer. This possibility would be difficult to accomplish with discrete matching layers that usually are less than a half-wavelength in thickness (nominally a quarter wavelength for single layer matching). This would be mechanically very fragile.

Therefore, an attractive transducer fabrication approach suggests itself using several of the ideas developed above. For a transducer array having one or more elements, each element attachment substrate could be the tapered matching construct with its thickness extended by longer micro-tapered constructs. The complete matching layer could have flat (but micro-grooved or pyramided) mounting surfaces for each element of the overall array. Such an overall matching layer construct could be made thick enough for mechanical integrity, unlike "quarter-wave" matching layers. The micro-tapered constructs onto which the array element ceramic is bonded could be filled with an appropriate epoxy-Tungsten (or other composite) material approaching the acoustic impedance of the ceramic. The micro tapered constructs would then taper the impedance down to that of the 3-D prototyping polymer. Such a construct would also allow lens fabrication for each element out of the same polymer (if required). This leaves another (but not larger) impedance discontinuity between the front surface of the polymer and the water transmitting medium into tissue. Note that a front surface of more micro-tapered constructs can be programmed into the fabrication process. The resulting front surface, grooved or pyramided, would fill with water allowing a gradual tapered continuity between the impedance of the prototyping polymer and water. If the resulting micro-depressions in the front surface result in excess air trapping, these can be filled with silicone rubber compounds having acoustic impedances near water.

Thus, tapered matching layer constructs can be designed for optimum acoustic impedance matching while also providing a very useful framework and substrate for fabrication of the array itself. The finished product, with all elements attached on the back surface, would then be treated as a single large diameter transducer element for simplified mounting into a much simpler frame compared to the multiple constructs necessary with discrete layer matching processes. Such a system would allow tapered impedance matching all the way from the transducer ceramic elements down to water with the added benefit of allowing lensed array elements.

And finally, for large diameter arrays exceeding the size restrictions of the prototyping polymer tank, the matching layer and overall frame onto which the matching layer-transducer construct might be mounted, can be fabricated in segments bonded together to produce the overall transducer design. In this method, polymer use, which can be expensive, can be minimized in structural sub-elements fabricated with thin ribs on the back forming closed honey-comb like compartments when all segments are "tacked" together. These compartments can then be filled with a strong epoxy thus providing waterproof bonding of all sub-elements and very strong structural integrity with a minimal use in prototyping polymer. Both the fabrication of smaller sub-elements and the minimization of prototyping polymer can result in very significant cost and time savings with no loss in structural integrity.

Such an overall matching and fabrication "system" would comprise very complex "local geometries" but these add no extra cost to the fabrication process once the 3-D design is programmed into the 3-D prototyping "solid-works like" software.

Evaluation of Element Mechanical Failure

Different compositions of piezoceramic material were evaluated to determine their ultimate pressure output limits prior to failure. Elements were positioned in a water bath with the front surface in contact with the water and enclosed in a small housing to ensure air backing of elements. A capsule hydrophone was positioned facing the transducer with 10 cm distance from the transducer surface. The element was attached to a voltage gain network and class D amplifier to apply up to 2400 $V_{pp}$ on the element. The amplifier is controlled by a field-programmable gate array logic board. Each element was first driven with a base signal of 10 $V_{pp}$ to measure the output under low amplitude conditions. The element was then driven for 10 seconds with a high amplitude signal of 10 cycles at a PRF of 1 kHz. The base signal was then reapplied to ensure the pressure output was the same. This was repeated, incrementing the test voltage each time until the base pressure output from the element was reduced. This process was also repeated to test the elements with acoustic lens with and without matching layers to compare with the bare elements in direct contact with water.

Figure 11:
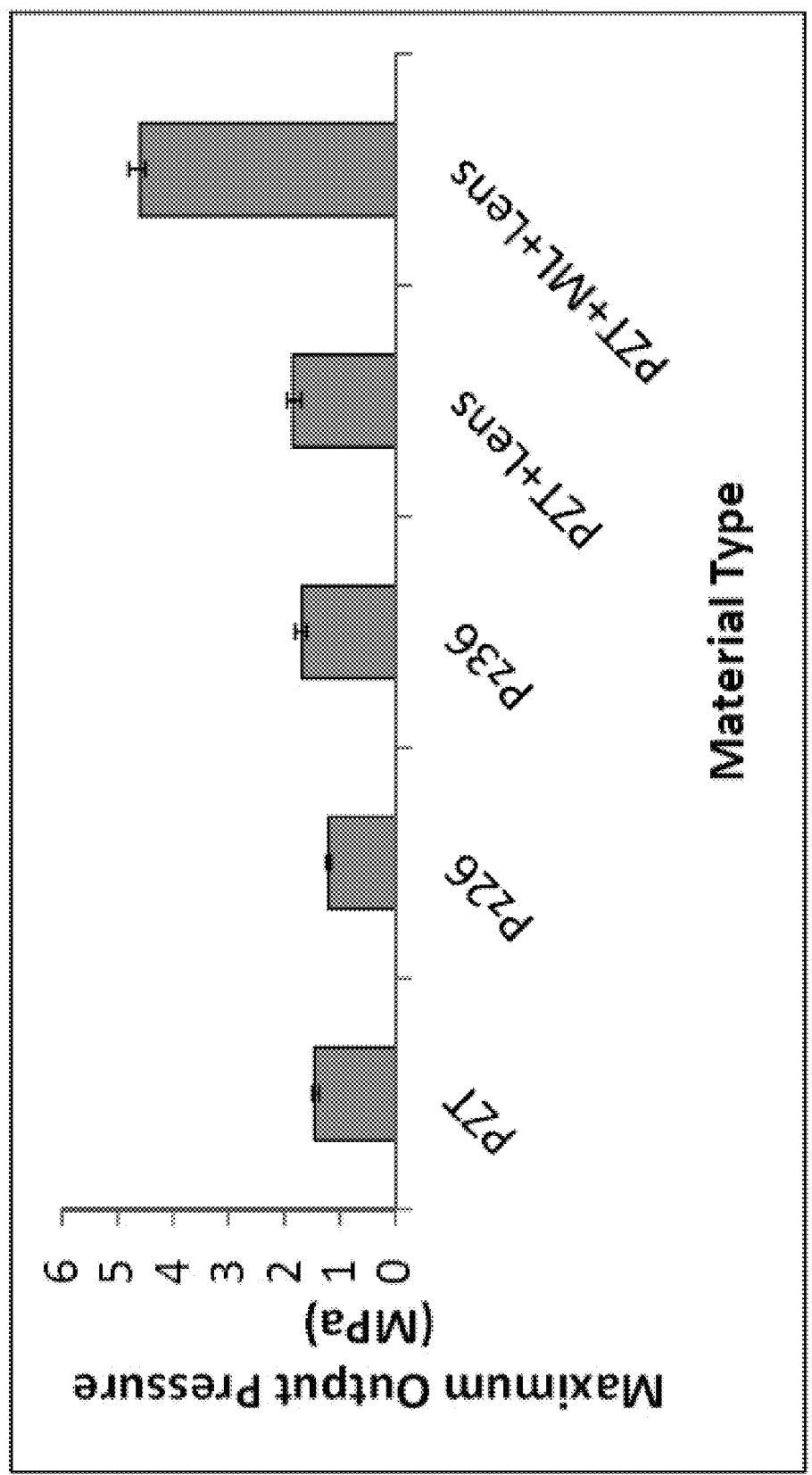
FIG. 11 illustrates maximum element surface pressure prior to failure with 10 cycle pulses applied at a 1% duty cycle. All types of PZT tested had similar failure points without matching layer. Each measurement is the mean of 3 samples, with the error bars showing the range of failure surface pressure. A consistent failure pressure for the elements with matching layer was not determined; the bar represents the highest estimated surface pressure level from the elements. Thus, 2000 $V_{pp}$ was considered a safe limit to drive 1 MHz elements with matching layer.

For each type of transducer element, n=3 elements were tested to determine the voltage at which the pressure output was irreversibly degraded. Element damage appeared as small chips in the back surface of the element, most often occurring near the center. This pattern suggests damage by lateral or radial resonances in the PZT material. This damage was evident in PZT, PZ26, and PZT with lens at similar drive voltages around 1000 $V_{pp}$ and an estimated surface pressure of 1.3-1.8 MPa. FIG. 11 illustrates the maximum element surface pressure prior to failure with 10 cycle pulses applied at a 1% duty cycle. All types of PZT tested had similar failure points without matching layers. Each measurement is the mean of 3 samples, with the error bars showing the range of failure surface pressure. A consistent failure pressure for the elements with matching layer was not determined; the bar represents the highest estimated surface pressure level from the elements. Thus, 2000 Vpp was considered a safe limit to drive 1 MHz elements with matching layer. In PZ36 material, which has a lower lateral coupling coefficient and lower impedance, no visible signs of failure were observed. However, element output decreased drastically at a similar drive voltage and pressure to the aforementioned materials. In all other elements, the occurrence of fractures was accompanied by concomitant decrease in pressure output and loss of resonances in the electrical impedance curves.

The PZT+matching layer+lens configuration did not incur irreversible damage up to 2000 $V_{pp}$, even when driven at this voltage for 300 seconds. Some decrease in the voltage input and pressure output was observed vs. time, possibly because of self-heating and detuning of the element. The lens unfortunately provides good thermal insulation from the water bath, and thus active cooling might be necessary in applications were high average power output is a requisite. Average power density for tests with the elements with matching layer/lens during maximum driving conditions was 7.8 W/cm$^2$, although it decreased to 5.9 W/cm$^2$ after 300 seconds driving due to this detuning. The element pressure output and impedance recovered to their original values after the ceramic returned to ambient temperature.

Design of a Transducer for Histotripsy Thrombolysis

Transducer Specifications

As the following is an example for the therapy transducer design and construction using rapid-prototyping method. The transducer is designed for treatment of deep-vein thrombosis (DVT) in the femoral veins. This transducer is coupled to the leg by a water bath and controlled by a 3-axis motorized positioner. The therapy transducer can be integrated with an ultrasound imaging system that is used to monitor and guide the treatment.

In order to obtain adequate images of vessels, it can be necessary to position the ultrasound imaging probe as close as possible to the target. In an example where the probe footprint is 50 mm×8 mm, the elements must fit around this geometry. The transducer working distance is determined by the estimated vessel depth of 1.5 cm in the in-vivo porcine model. The focal dimensions of the transducer are determined based on the target size. The target size for the femoral thrombolysis transducer is defined by the vessel diameter which is about 6 mm in diameter. For focused transducers, the axial dimension defines the longest dimension of the focus, which should be less than 6 mm to ensure cavitation occurs solely in the vessel lumen. Furthermore, based on previous histotripsy studies, the focal gain should be >30 to generate enough pressure to generate a cavitation cloud.

Transducer Modeling

Several equivalent circuit models exist for piezoelectric ceramics operating in thickness mode. The model applied here, developed by Krimholtz, Leedom, and Matthaei (KLM), is considered the most intuitive from a time-domain standpoint, representing the mechanical thickness of the transducer by transmission lines. This formulation is amenable to a transfer matrix approach, where several matrices, each describing an electrical or mechanical part of the transducer, can be multiplied to determine the pressure-voltage transfer function. This method was developed by Van Kervel and Thijssen, and has been further developed by Marechal et al. for calculations with a spherically-curved acoustic lens. These works were followed to develop the basic theory for the KLM model. Additionally, models of the amplifier, transducer cable and matching networks were included on the electrical side of the network, and for the acoustic side, equations for elliptical lens were developed to determine the impedance and surface pressure profile. Note that although surface pressure measurements are provided, these are not directly applicable to the experimental results or propagation model, as the diffraction from the element edges generally creates a spatially-dependant pressure across the element surface. More applicable is the element surface velocity, $u_s$, which is used as the actual input to the Rayleigh integral. However, surface pressure is given here to give an idea of the pressure gain afforded by focusing as $p_s = u_s \rho_l c_l$.

Figures 12D, 12E, 12F:
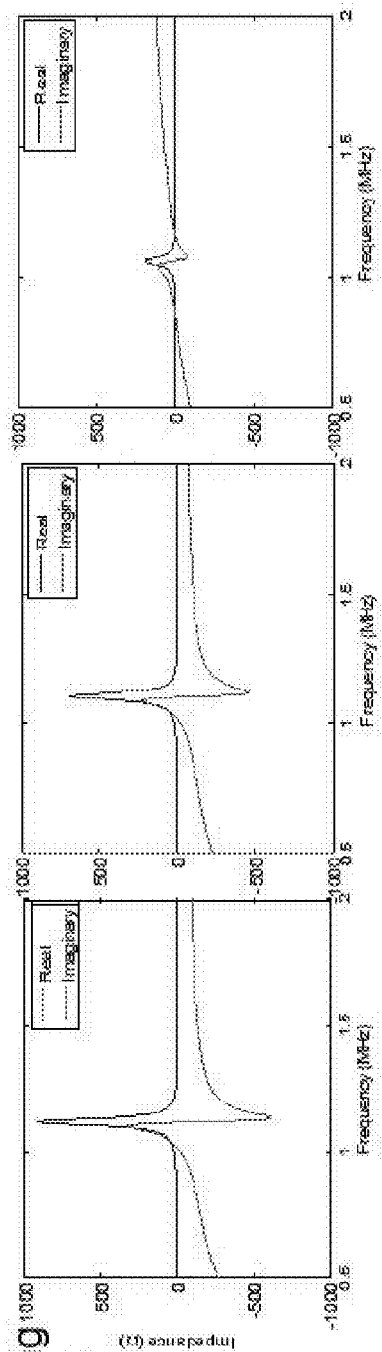

Each element in the transducer was made from a modified PZT-4. Given the specification that the transducer fit around the imaging transducer, and that the transducer focal length was 5 cm, 2-cm diameter disk-shaped elements were chosen with a thickness resonance of 1 MHz. The properties for different PZT formulations are shown in Table III. For the modeled results, properties for PZT-4 are used. For an element of the specified geometry and parameters, the element electrical impedance for an element coupled to water directly as a load and air as a backing is shown in FIGS. 12A-12F. In FIGS. 12A-12F, impedance traces of elements without (FIGS. 12A-12C) and with (FIGS. 12D-12F) matching layers/lens are shown. The element impedance is shown directly connected to the element terminals (FIGS. 12A and 12D), the end of a 2-meter cable attached to the elements (FIGS. 12B and 12E), and at the input to the voltage gain network (FIGS. 12C and 12F).

TABLE III

Material properties of the piezoelectric materials in this study, as well as the matching layer and lens parameters for this transducer.

|  | PZT-4 | PZT-8 | Pz36 | Matching Layer | Lens |
|---|---|---|---|---|---|
| $\epsilon_s$ | 650 | 600 | 300 | N/A | N/A |
| $k_T$ | 0.45 | 0.45 | 0.5 | N/A | N/A |
| P (kg/m$^3$) | 7550 | 7500 | 5500 | 5500 | 1200 |
| $c_0$ (m/s) | 4590 | 4590 | 2600 | 1240 | 2560 |
| $Z_0$ (MRayl) | 34.6 | 34.4 | 14.3 | 6.8 | 3.1 |

The impedance with a matching layer is $Z_m$=6.8 MRayl, close to the geometric mean of 7.2 MRayl, and a lens layer $Z_l$=3.1 MRayl. The element impedance at 1 MHz with 2 meter BNC RG-174 cable is simulated to be 61-107 jΩ. A voltage gain of 4 is desired to transform the maximum voltage on the element from 400 V to 1600 $V_{pp}$. The voltage network C and L values given in Appendix A are C=1.3 nF and L=9.7 µH. Available values of 1 nF and 11 µH give G=3.5. Applying this to the simulation, the impedance as seen by the amplifier for one element becomes 20.5Ω, within the limits of the amplifier. If this final impedance value is outside the limits of the amplifier, the designer must choose a lower gain value for the network, or alter the element in another way to raise the initial impedance.

Figure 13:
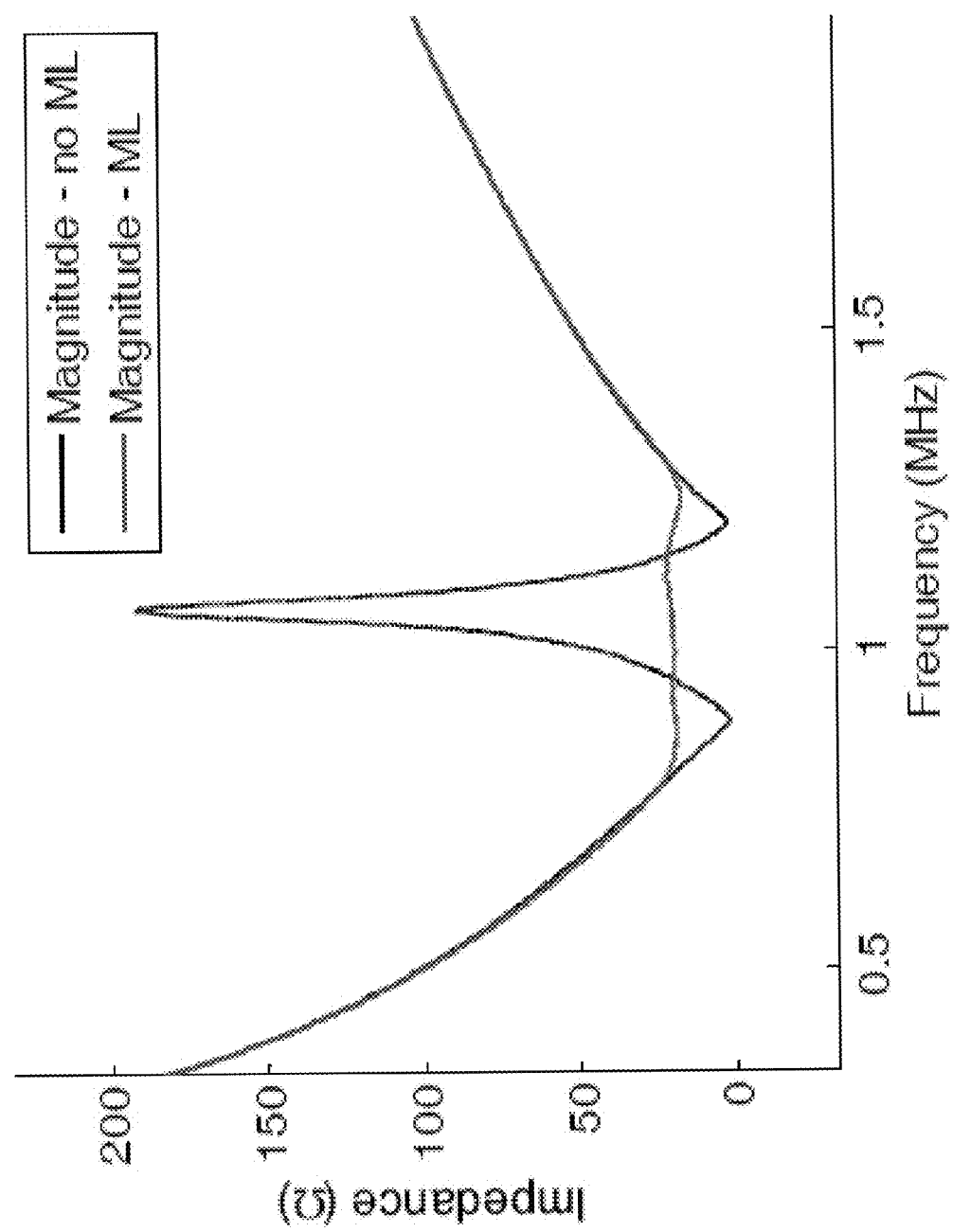
FIG. 13 illustrates impedance magnitude of a 1 MHz element with voltage network and cable with and without matching layer and lens.

Note that with addition of the voltage network to the element, the impedance remains fairly constant across the bandwidth of 0.8-1.3 MHz for the element with matching layer and lens (FIG. 13). Without the matching layer or lens, the impedance varies with small changes in frequency from only 4 ohms at 0.86 MHz up to a peak of nearly 200 ohms at 1.06 MHz and back down to about 4 ohms at 1.16 MHz. This also means the bandwidth is narrow at the low-impedance positions (FIGS. 14A-14F). The flattening of the impedance curve by the matching layer and lens leads to a more consistent output vs. frequency.

Similar surface pressures can be achieved by transducer elements with and without matching layers, but the element without matching has a ringup time of more than 20 cycles to reach the same steady state amplitude as the matched element reaches in 3-4 cycles. As only the largest amplitude cycles of the pulse will contribute to bubble cloud generation, the long ringup time for the unmatched transducer will consequentially increase the undesirable heating as a side-effect of the treatment and make it inefficient. Due to the increased bandwidth of the transducer with matching, very short pulses with high amplitude can be produced. The impulse response of two equivalent transducers with and without matching layers are shown in FIGS. 15A-15D. Note that the peak voltage into each element is nearly identical, but the matched transducer peak pressure output is 2.9 times larger than the unmatched case. Thus, the voltage applied to the unmatched element is considerably higher for equivalent output. The peak-peak voltage with matching layer/lens is about 2.1 $kV_{pp}$ to achieve 6 MPa surface pressure, while the unmatched element requires >9 $kV_{pp}$ to achieve the same (FIGS. 16A-16D). Another result of matching is reduced internal stress in the element for a given surface pressure in the load, as a greater percentage of the resonant wave each cycle is transmitted to the load medium. These factors all suggest that acoustic matching is important to obtain short, high-amplitude pulses with a controllable output.

Propagation Model

A propagation model based on the Rayleigh integral was implemented to determine the focal characteristics of the transducer, including the focal dimensions and focal gain for transducers. This equation defines linear propagation with excellent accuracy. Histotripsy can be highly dependent on nonlinear propagation, thus the linear propagation model is a simplification and does not accurately predict the waveforms developed at the focus. However, the cavitation cloud and peak negative pressure of the focal waveform occur over a similar region to that predicated by linear theory. Thus, while this model will not provide the detailed waveform, it can be applied to determine the region where cavitation can be expected. Additionally, the linear focal gain can be calculated which provides an indication based on previous histotripsy transducers whether sufficient pressure can be generated. Previous histotripsy transducers used in-vitro and in-vivo have focal gains ranging from 40-90.

Propagation models were developed for point sources, rings, disks, rectangular plates, and spherical segments with round and rectangular aperture. If a single element is being modeled, its dimensions are established and then the geometry is constructed of individual point sources with no greater than λ/2 spacing to ensure accuracy throughout the entire pressure field. If multiple elements are to be simulated, the center position of each element is also input, and the model then produces copies of the transducer element at each location. This allows accurate simulation of transducer geometries with F#=total aperture/focal length>0.5. The simulation is performed at the transducer center frequency, meaning it is accurate for CW or long bursts. Short burst simulation requires a transient model.

Each element in the transducer is focused to a common focal point. The focal gain of a single, spherically-focused transducer element can be estimated by the ratio of Rayleigh distance to focal distance:

$$G_f = \frac{z_r}{z_f} = \frac{A}{\lambda z_f}, \tag{8}$$

where A is the active area of the transducer element. The histotripsy transducer used in preliminary studies of thrombolysis had $G_p$=42. However, this transducer had a focal dimensions which exceeded the target vessel diameter and had too great of a focal length, causing difficulty placing an imaging guidance probe in the vicinity of the vessel. Thus, a transducer with similar focal gain but with smaller focal dimensions was required to improve the imaging and therapy outcome. Additionally, the transducer was required to house an available linear array imaging probe which is suitable for vascular imaging. This probe had a footprint of 50 mm×8 mm. As such, the 2-cm therapy elements for the thrombolysis transducer were positioned around a central port or hole (see FIGS. 5A-5B) as closely as possible. At 1 MHz, the transducer has $G_f$=33, meeting the specification. The previous design was capable of much greater pressure output than was necessary to achieve cavitation in-vivo, and as such, this gain should be sufficient to treat vessels through 1-2 cm overlying tissue. Additionally, the focal dimensions at 1 MHz are small enough to target the 6-7 mm diameter vessels. While greater gain can be obtained at higher frequencies (Table IV), the smaller focal dimensions will increase acoustic attenuation and extend the treatment time.

Figure 17:
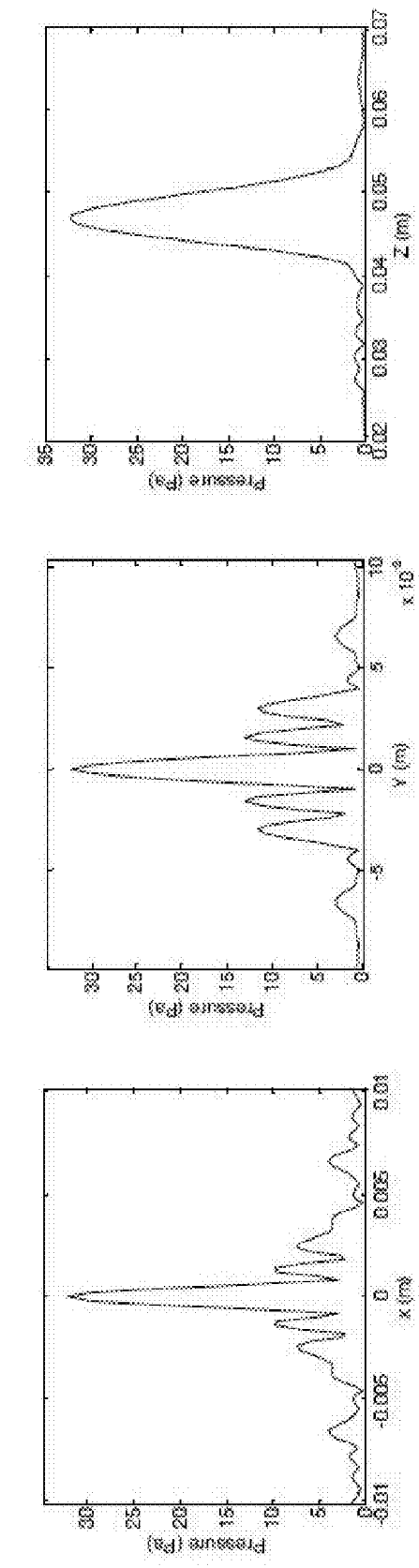
FIG. 17 illustrates one-dimensional beam profiles corresponding to FIG. 21. (Left) X transverse pressure profile. (Center) Y transverse pressure profile. (Right) Z axial pressure profile.

The large spacing between the elements along the Y-axis due to the imager port cause substantial grating lobes around the focus (FIG. 17). These grating lobes can have amplitude around ⅓ the peak pressure amplitude. However, it has been shown that lesions can be accurately created only within the main focus, even in the presence of grating lobes which are greater than ½ the amplitude of the main beam. Thus, it is expected that cavitation will be confined to the main beam dimensions.

TABLE IV

Comparison of focal dimensions and gain between 3 transducers of the same geometry but different frequency.

| | −6 dB X (mm) | −6 dB Y (mm) | −6 dB Z (mm) | Focal Gain |
|---|---|---|---|---|
| 1 MHz | 1 | 1.2 | 6.6 | 33 |
| 1.5 MHz | 0.7 | 0.8 | 4.2 | 49 |
| 2 MHz | 0.5 | 0.6 | 3.3 | 66 |

Transducer Construction

Several embodiments of a thrombolysis transducer were constructed. In the first designs, 8 spherical segments of PZ26 material were used without matching layer in 8 subhousings. While this minimized the size of the device, difficulties in preventing electrical problems at voltages >800V required a larger design. The second generation device comprised one larger housing in which all the spherical elements could be properly seated and isolated electrically. This device was initially successful in generating cavitation in vivo, but the driving voltages necessary were near the mechanical failure limit for the ceramics as determined above. Fragmentation was evident in the back face of multiple elements after about 600 seconds of operation. Thus, the final design was constructed with flat disc elements and formed lenses with a matching layer interface (as shown in FIGS. 5A-5B).

The overall aperture of the final transducer was 7.3 cm×8.6 cm. The radius of curvature for the transducer was chosen to be 5 cm to position the imaging probe in the center as close to the target as possible. The central port for the ultrasound imager was designed to hold a 10 MHz linear array or a 12 MHz phased array probe for high frequency imaging of the vasculature. All 3 transducers were printed on a 3D printing system, which was chosen because the material had low attenuation and high sound speed compared materials on other systems, and adequate printing resolution.

Transducers were constructed with piezoelectric elements made from the PZT4 material. For the first and second generation transducers without matching layers or lens, a hole in the housing for the acoustic aperture is placed such that the elements can be sealed, either on the front or side surface, into the housing. Non-corrosive room temperature vulcanizing (RTV) rubber can be used as a sealant. Two wires can be soldered onto the element front and back silver electrodes. A silver-bearing solder (96/4 Sn/Ag) can be used to prevent dissolution of the electrode during soldering. Soldering was performed at 250° C. for no greater than 3 seconds per electrode. This minimized the possibility of oxidation of the joint and depolarization of the element. The wires were soldered to either RG-58, RG-174, or RG-316 coaxial cable terminated by Bayonet Neill-Concelman (BNC) connector. The cables were run through ports in the housing, and sealed with flexible polyurethane.

Figure 18B:
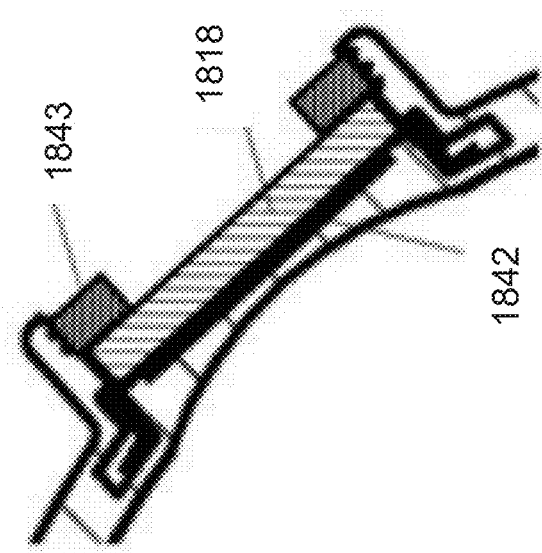
FIGS. 18A-18B illustrate cross-sectional detail of a piezoelectric element housing with lens. The left image shows the housing prior to placement of the element and matching layer, and the right image shows the final state once the element is in place.
Figure 18A:
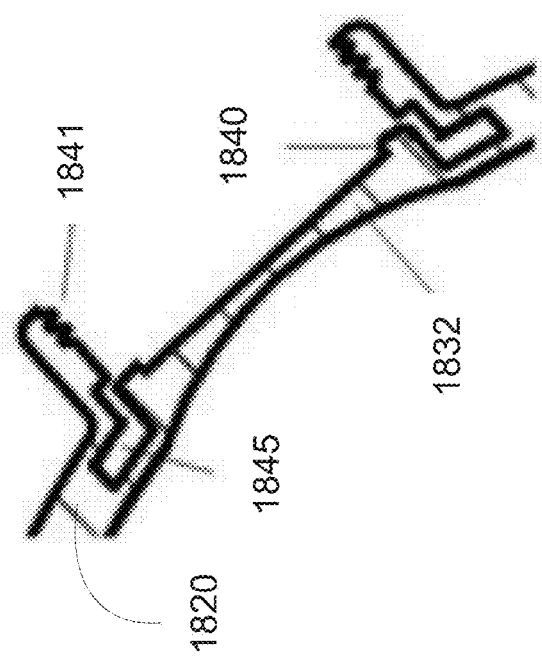

In some embodiments described herein, transducers with matching layers and lens can be constructed with the lens built into the housing. FIG. 18A illustrates an acoustic lens 1832 incorporated into the rapid-prototyping housing 1820, along with other features incorporated into the rapid-prototyping housing such as matching layer standoffs 1840 and compression threads 1841. Matching layer overflow well 1845 can be configured to contain an overflow of matching layer material in the event that too much material is applied. In FIG. 18B, the matching layer 1842 and transducer element 1818 are held in place against the acoustic lens with compression ring 1843 screwed into compression threads 1841. On the surface of the lens facing the element, three small standoffs can be printed to create a gap with the thickness of the matching layer. A small volume of matching layer material can be mixed, as described above, and dispensed as a droplet in the center of the back lens surface. The element can then be pressed onto the standoffs. Excess material can then run into adjacent wells to prevent the material from overflowing onto the back of the element and causing electrical breakdown around the element at high driving voltage. The pressure may be applied by hand, or pressed by a compression cap which screws into the element housing behind the element and applies continuous pressure on the element back surface. All elements can be populated into the housing in this manner, and allowed to cure for at least 24 hours before any measurements are made. Wiring and sealing can be performed in the same manner as described for transducers without matching layers or lens.

Transducer Comparison with Model

Figure 19:
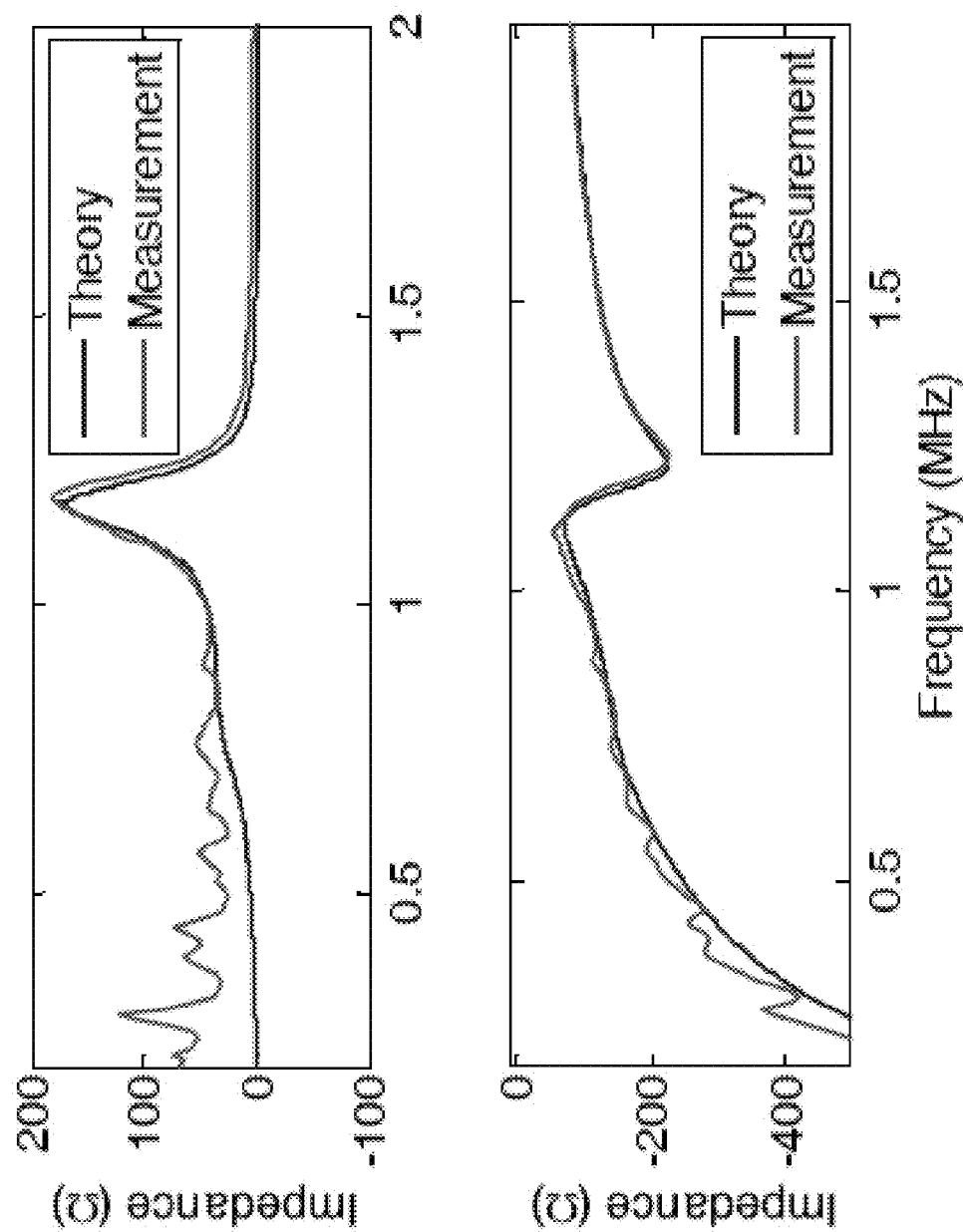
FIG. 19 illustrates comparison of simulated and experimentally measured electrical end-of-cable impedance for an element of the thrombolysis transducer.

For modeling of the third generation transducer, a 2-cm diameter disc made from PZT-4 as described above with a matching layer. The modeled and measured electrical impedance curves of a single element with matching layer and lens are provided in FIG. 19. Good agreement is observed between measurement and the model near resonance when the matching layer thickness is chosen appropriately. For this transducer, the model indicated that the matching layer was 45 μm thicker than $\lambda/4$, causing the higher impedance curve at frequencies >1 MHz. The error in matching layer thickness is likely due to the printer resolution limit, which prints the transducer housing in 100 μm increments. However, the impedance curves were remarkably consistent between elements. For n=8 elements, the impedance at 1.0 MHz was 48.3+/−1.5Ω for the real part and −94.6+/−3.3 jΩ for the imaginary part (mean+/−standard deviation). For comparison, the impedance given by the model is 44-102 jΩ at 1 MHz with the matching layer thickness=$\lambda/4$+45 μm. At low frequency, there is some deviation of the model from the measurements, caused by radial (lateral) modes in the element, which are not considered in the 1-D KLM model.

A two-dimensional pressure map was acquired by scanning the field with a capsule hydrophone. The peak positive pressure values from a 10-cycle burst were used to record the pressure amplitude at each point in the field. The lateral −6 dB beamwidth at z=50 mm from the transducer face was 5.1 mm in the simulation and 5.3 mm measured. Near the transducer surface (z=7.5 mm), the beam width was 17 mm when simulated and 15.9 mm when measured. These measurements suggest that the acoustic lens provides nearly ideal focusing similar to a spherical transducer segment.

The beam profiles of the full transducer (all 8 elements driven) was also measured and compared with simulation. The X×Y×Z−6 dB pressure beam width for the simulation was 1.0×1.2×6.6 mm for the 1 MHz transducer. When measured with the capsule hydrophone, the beam width at the focal plane was 1.0×1.3×6.9 mm. These measurements are also in agreement with the simulated values.

Transducer Output Pressure

A fiber-optic probe hydrophone (FOPH) was used to measure focal pressure waveforms of the completed transducer. The hydrophone had a bandwidth of 50 MHz, an active element of 100 μm diameter, and a low-frequency sensitivity of 0.35 mV/MPa. The sensitivity of the hydrophone varies with frequency due to diffraction from the fiber tip. A piezoelectric hydrophone with known frequency response was used to find the frequency response of the hydrophone. A deconvolution procedure was written to correct for the hydrophone frequency response to obtain accurate pressure waveforms. The transducer focal pressure was measured in degassed water up to the point where cavitation occurred. Beyond this pressure level, measurements were recorded in a cavitation-resistant liquid.

Figure 20A:
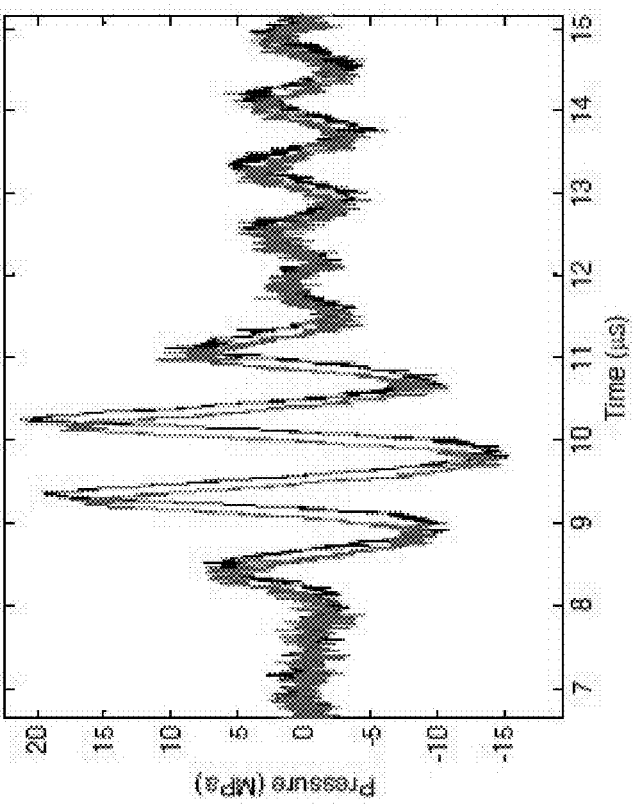
FIGS. 20A-20B illustrate (Left) waveforms received at the transducer focus by each of the eight elements in the therapy transducer. (Right) Focal pressure estimated by summing all eight waveforms recorded without (red) and with (black) phase error correction.
Figure 20B:
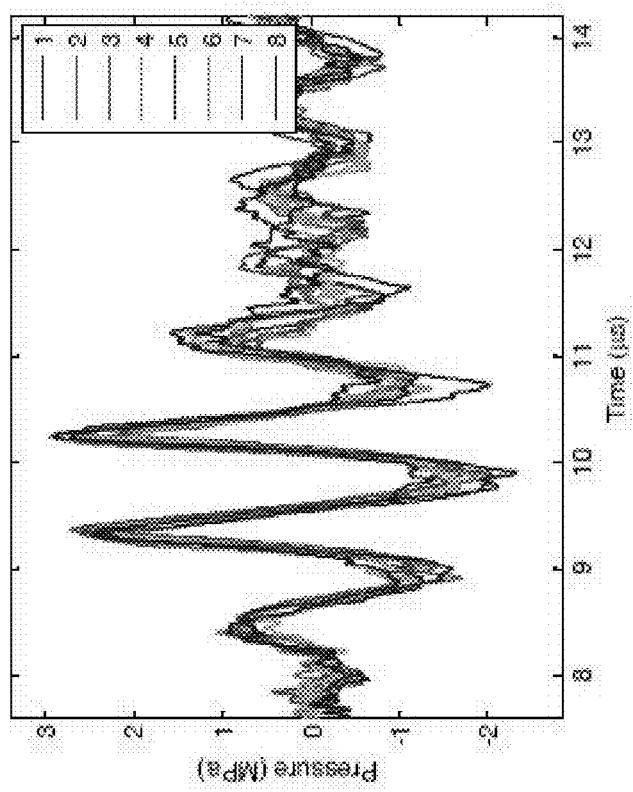

Ideally, all lenses are constructed such that each lens surface is equidistant from the transducer focus. If this is not the case, a phase delay will exist between elements. Depending on the phase delay, the pressure wave from each element may constructively or destructively interfere at the focal point. One criteria for the acceptable phase shift between elements for focusing is <λ/8. To determine the phase error between multiple elements in the transducer, a capsule hydrophone was positioned at the transducer focus, and each element was driven individually. The eight waveforms received are shown in FIGS. 20A and 20B. The time delay difference between the most leading and lagging elements is 80 ns, or λ/12. This phase error corresponds with a decrease of 10% in the focal peak-peak pressure under linear conditions compared to ideal element alignment.

Figure 21B:
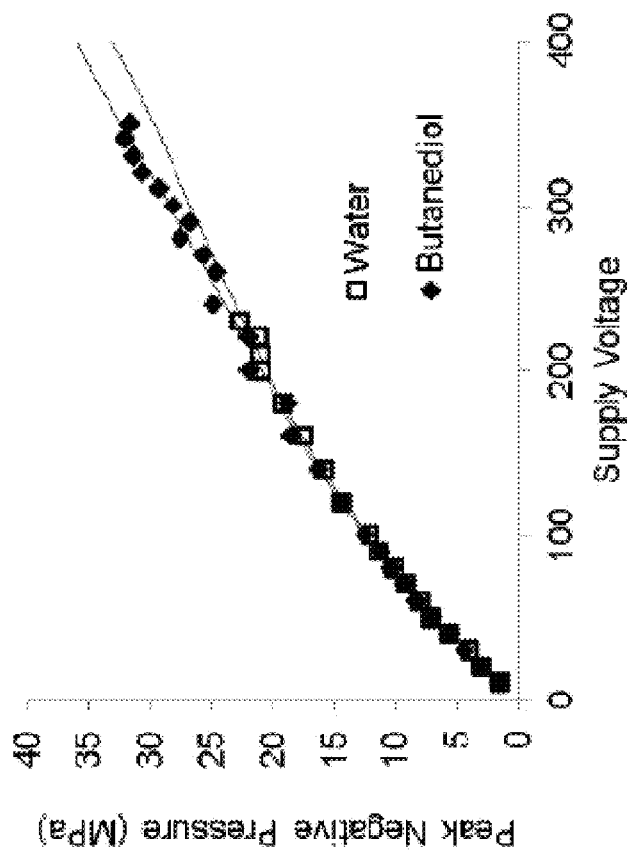
FIGS. 21A-21B illustrate (Left) focal pressure waveform recorded by FOPH at 80% drive voltage—about 1280 $V_{pp}$. (Right) Peak negative focal pressure vs. DC supply voltage.
Figure 21A:
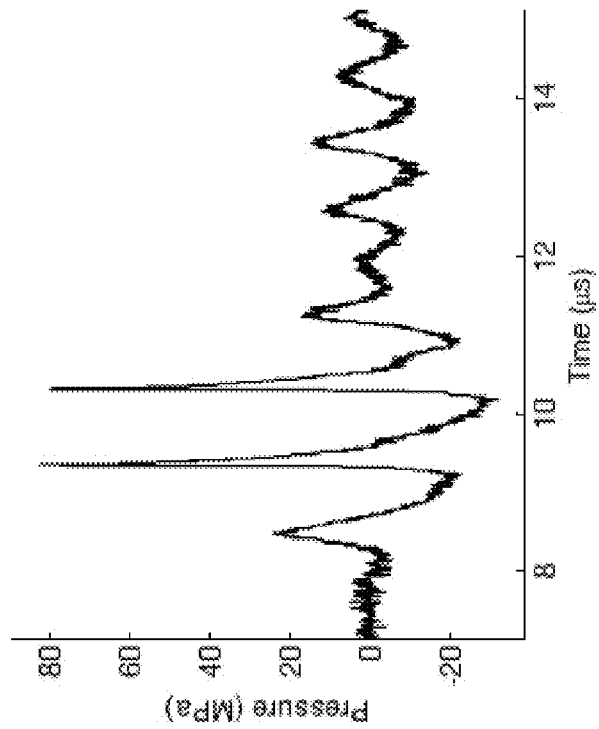

FIGS. 21A and 21B show the pressure waveform at 80% drive voltage to the transducer, with the peak negative pressure reaching 31 MPa and the peak positive pressure reaching 85 MPa. These results compared well with measurements in water up to 50% drive voltage. Due to cavitation on the hydrophone tip, pressure waveforms greater than 2 cycles could not be acquired at large pressure amplitudes.

Transducer Testing in Histotripsy Application

In order to determine the cavitation potential of the constructed transducers, bubble clouds were imaged by high speed photography under different pulse length and pulse repetition frequencies. The lowest peak-negative pressure values at which cavitation is observed each pulse was defined as the cavitation cloud threshold for a specific set of acoustic parameters in degassed water. The pressure levels are given in Table V. As either pulse repetition frequency (PRF) or pulse length are increased, the bubble cloud can be sustained each pulse at a lower pressure level. At the highest power setting, a cavitation cloud is generated at 19.5 MPa peak negative pressure. While this is somewhat higher than other histotripsy transducers, it is expected that transducers with high curvature similar to this design will have a greater negative pressure threshold than those with lower curvature because of nonlinear propagation. At the lowest PRF and pulse length, cavitation clouds do not appear consistently until $p_- = -30.7$ MPa.

TABLE V

Pressure (MPa) above which a cavitation cloud occurs each pulse at different pulse lengths and pulse repetition frequency (PRF).

|  |  | PRF (Hz) | | | |
| --- | --- | --- | --- | --- | --- |
|  |  | 1 | 10 | 100 | 1000 |
| Pulse Length | 2 | 30.7 | 30.7 | 30.7 | 24.6 |
|  | 3 | 30.7 | 30.7 | 26.2 | 23.9 |
|  | 5 | 29.3 | 29.3 | 23.2 | 21.6 |
|  | 10 | 29.3 | 28.5 | 22.4 | 20.3 |
|  | 20 | 29.3 | 28.5 | 22.4 | 19.5 |

Tissue ablation in ex-vivo porcine kidney was achieved to confirm the performance of the histotripsy transducer. Lesions were made using 5 cycle pulses at a 100 Hz PRF in the porcine kidney cortex. The kidney was cast in 10% gelatin in a polycarbonate housing with an acoustic window for sonication. The transducer focus was positioned in the kidney cortex and treated for 30 seconds (3000 pulses) each point. Four lesions were generated. This result suggests that the transducer is capable of performing histotripsy with similar results to previous studies.

Designs and methods for constructing therapy transducers capable of performing histotripsy thrombolysis were developed in this study using additive manufacturing. Several techniques have been explored to construct transducers of single- and multiple-element configurations. More than 20 transducers for various applications in histotripsy including thrombolysis have been designed. The most effective transducer designs incorporated 1 small elements with matching layers and lens. This design made it possible for the amplifier to drive at high voltage through a voltage transforming network, and prevented mechanical failure of the transducer under high pressure output.

Rapid-prototyping of transducers holds several key advantages for developing transducers in a research setting and for low volume capital equipment. First, the overall cost and time to produce a prototype is greatly reduced compared with a conventional machining process. For injection molded parts, the cost of molds and lead times for mold production also are prohibitive for research and development and low volume capital equipment. Although materials for a rapid-prototyping system can be expensive per unit weight, since they are built additively, no material is lost during manufacture. There is also no penalty for introducing additional complexity into the design. For instance, to reduce cost of material, a hollow frame can be adopted with a strut pattern for rigidity. Whereas in machining it is often prudent to reduce cost by requiring as few cuts as possible to finish the piece; and in injection molding, complexity adds to mold cost. While this can be to the benefit of the designer, it can also be a pitfall. If such a part is to be mass produced, it may require injection molding or other techniques with more significant geometric limitations. In such a case, some features of the parts may have to be redesigned for these production modes. However, for the purposes of research or low volume capital equipment, where only a few units are typically developed or manufacturing volume does not justify expensive injection mold tooling, this is generally not a concern.

The materials in such designs are generally not equivalent in mechanical nature to their cast or extruded counterparts. While some machines, such as FDM, utilize ABS or polycarbonate to produce prototypes, the layering of the materials does not produce parts with the same strength as a solid piece. Furthermore, other machine types, particularly those which use photopolymers, require proprietary formulations which do not particularly match the properties of any conventional material, but they encompass the same range as plastics. Some machines, such as the 3D printer used in this study, can in fact produce composites with continuously variable elastic moduli. Several of these materials were characterized in this study for the purpose of identifying those which would be suitable as acoustic parts. Several materials were found to be suitable, but the material produced by the SLA machine provided the proper combination of low attenuation and high sound speed to produce lens with low loss. The 3D printing system tested in this study, had a step resolution of 16 μm, which could have provided more precise fabrication of matching layers, and can be employed transducer designs and construction. Materials for fabrication of transducer designs with other systems must provide equal or more precision and equal or lower acoustic transmission losses. As the range of materials which can be used by rapid-prototyping machines grows, it may become possible to print the ceramic elements, matching layers, and electrodes of the transducer, simplifying the processes and design possibilities even further.

In focused ultrasound thermal therapy, the ceramics are generally capable of operating within the required pressure output range needed to cause tissue ablation. However, histotripsy requires focal pressures significantly higher than thermal therapy, and the ceramics in early therapy transducers were stressed to their mechanical limits. The surface pressure necessary to perform histotripsy with boiling is about 500 kPa amplitude, which produces a peak negative focal pressure of 14 MPa from a transducer with linear focal gain $G_f$=49. Based on tests performed in this study, the transducers are within the limits of mechanical failure. However, cavitation-based histotripsy requires focal pressures of >20 MPa at the focus, which required >2 MPa surface pressure for the thrombolysis transducer—above the limit of the bare ceramics. Additionally, the necessity of short pulses meant significantly greater bandwidth was needed. The matching layer/lens combination allowed the transducer to be made with a small aperture and focal gain and still provide sufficient focal pressure. The design demonstrated that the matching layer prevents the buildup of stress due to strong resonance within the ceramic element when highly mismatched to the load. This allowed the transducers to be driven to nearly 3 times the surface pressure prior to failure. Although this design extended the mechanical limits of the transducer elements, the insulation provided by the lens prevented dissipation of heat in the element at higher driving powers. Even with a duty cycle of 1% at 2000 $V_{pp}$ input, the elements reached nearly 70° C. after driving for 300 seconds. This causes a change in the sound speed in the ceramic material and a shift in the resonant frequency. As a result, the output is lowered, and the total power into the element is limited until it returns to ambient temperature.

What is claimed is:

1. A method of designing and manufacturing an ultrasound system, comprising:
designing a transducer housing shell to a desired geometry and a plurality of acoustic focusing lenses integral to the transducer housing shell such that the transducer housing shell and the plurality of acoustic focusing lenses are each designed in a 3D computer aided design software; and
constructing the transducer housing shell and the plurality of acoustic focusing lenses integral to the transducer housing shell wherein the transducer housing shell and the plurality of acoustic focusing lenses are each formed using a rapid-prototyping method.

2. The method of claim 1 wherein the designing step further comprises designing the transducer housing shell to a desired geometry so that a plurality of openings in the housing shell are aligned to converge upon a common focal point.

3. The method of claim 2 further comprising constructing a plurality of transducer element modules with the rapid-prototyping method, and inserting the transducer element modules into the openings of the transducer housing shell.

4. The method of claim 1 further comprising:
inserting a plurality of substantially flat, piezoelectric or piezoceramic elements, into the transducer housing shell so that ultrasound energy from the piezoelectric or piezoceramic elements converges upon a common focal point.

5. The method of claim 1 further comprising:
inserting a plurality of curved, piezoelectric or piezoceramic elements, into the transducer housing shell so that ultrasound energy from the piezoelectric or piezoceramic elements converges upon a common focal point.

6. The method of claim 1 wherein the rapid-prototyping method is selected from the group consisting of fused-deposition modeling, 3D printing, and stereolithography.

* * * * *